(12) United States Patent
Buettelmann et al.

(10) Patent No.: US 7,585,874 B2
(45) Date of Patent: *Sep. 8, 2009

(54) ARYL-ISOXAZOL-4-YL-IMIDAZO[1,2-A] PYRIDINE DERIVATIVES

(75) Inventors: Bernd Buettelmann, Schopfheim (DE); Bo Han, Shanghai (CN); Henner Knust, Rheinfelden (DE); Andrew Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 211 days.

This patent is subject to a terminal disclaimer.

(21) Appl. No.: 11/654,183

(22) Filed: Jan. 16, 2007

(65) Prior Publication Data

US 2007/0179178 A1 Aug. 2, 2007

(30) Foreign Application Priority Data

Jan. 17, 2006 (EP) .................................. 06100426

(51) Int. Cl.
*A61K 31/4353* (2006.01)
*C07D 471/02* (2006.01)

(52) U.S. Cl. ................. 514/300; 546/112; 546/113; 546/121; 514/277; 514/279; 514/299

(58) Field of Classification Search ............. 546/112, 546/113, 121; 514/277, 279, 299, 300
See application file for complete search history.

(56) References Cited

FOREIGN PATENT DOCUMENTS

| WO | WO 01/29015 | 4/2001 |
| --- | --- | --- |
| WO | WO 02/02557 A2 | 1/2002 |
| WO | WO 02/50062 A2 | 6/2002 |
| WO | WO 02/081474 A1 | 10/2002 |
| WO | WO 02/092086 A1 | 11/2002 |
| WO | WO 03/004027 | 1/2003 |
| WO | WO 2004/076452 A1 | 9/2004 |
| WO | WO 2005/123672 A2 | 12/2005 |

OTHER PUBLICATIONS

Database Chemcats Interchim intermediates 2005, "Chemical Library" XP002432244 accession No. 2005:1908499 RN= 478245-87-3 abstract.
Database Chemcats Interchim Intermediates 2005, "Chemical Library" XP002432245 accession No. 2005:1908498 RN = 478245-86-2 abstract.
McNamara et al., Psychobiology (1993), vol. 21, pp. 101-108.
Lam et al., Bioorganic & Medicinal Chemistry Letters (2003) vol. 13(10) pp. 1795-1799.
Wang et al., Journal of Fluorine vol. 111(2) pp. 241-246 (2001).
Roy et al., Synthesis, 2003 pp. 1347-1356.
White, et al., Journal of Organic Chemistry (1981), vol. 46(11) pp. 2273-2280.
Shi Shun et al., J. Org. Chem. Vol. 68 (2003) pp. 6810-6813.
Burke, et al., Journal of Natural Products, 1986, vol. 49, pp. 522-523.
Hamper et al., J. Agric. Food Chem. (1995), vol. 43, pp. 219-228.
Kumar, et al., Tetrahedron Letters, vol. 47, (2006), p. 1457-1460.
Hormi, Organic Syntheses Coll., vol. 8, p. 247 (1993) & vol. 66, (1988), p. 173.

*Primary Examiner*—Golam M Shameem
(74) *Attorney, Agent, or Firm*—George W. Johnston; Patricia S. Rocha-Tramaloni; Kimberly J. Prior

(57) ABSTRACT

The present invention is concerned with aryl-isoxazol-4-yl-imidazo[1,2-a]pyridine derivatives of formula I:

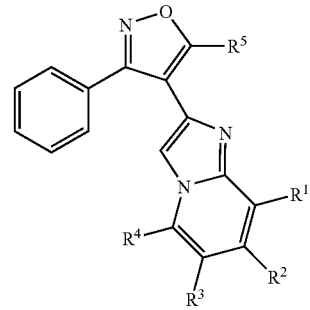

wherein
$R^1$ to $R^5$ are as defined in the specification and pharmaceutically acceptable acid addition salts thereof. This class of compounds has high affinity and selectivity for GABA A α5 receptor binding sites and might be useful as cognitive enhancer or for the treatment of cognitive disorders like Alzheimer's disease.

16 Claims, No Drawings

ARYL-ISOXAZOL-4-YL-IMIDAZO[1,2-A]PYRIDINE DERIVATIVES

PRIORITY TO RELATED APPLICATIONS

This application claims the benefit of European Application No. 06100426.3, filed Jan. 17, 2006, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR. It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides aryl-isoxazol-4-yl-imidazo[1,2-a]pyridine derivatives of formula I

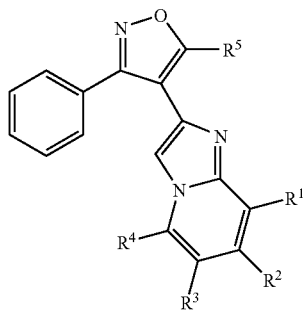

I wherein
R¹ is hydrogen, halogen, hydroxy, lower alkyl, benzyloxy or —O—(CH₂)—(CO)-5 or 6 membered heteroaryl optionally substituted by aryl or by lower alkyl;
R² is hydrogen, halogen, lower alkyl, lower alkynyl, amino, —NHC(O)—Rᵃ or —(CO)—Rᵃ;
R³ is hydrogen, halogen, cyano, lower alkyl, lower alkynyl, amino, —NHC(O)—Rᵃ, —(CO)—Rᵃ, -5 or 6-membered heterocycloalkyl in the 1-position, optionally substituted by =O or is a -5 or 6-membered heteroaryl in the 1-position;
R⁴ is hydrogen or -5 or 6-membered heteroaryl;
R⁵ is lower alkyl or cycloalkyl;
Rᵃ is lower alkoxy or NR'R", wherein R' and R" are each independently hydrogen, lower alkyl optionally substituted by hydroxy, lower alkynyl, —(CH₂)ₙ-cycloalkyl, —(CH₂)ₙ-5 or 6-membered heterocycloalkyl or —(CH₂)ₙ-5 or 6-membered heteroaryl; and
n is 0 to 3;

and pharmaceutically acceptable acid addition salts thereof.

The invention provides pharmaceutical compositions which comprise a compound of formula I or a pharmaceutically acceptable salt thereof and a pharmaceutically acceptable carrier. The invention also provides methods for the production of the compounds and compositions of the invention.

This class of compounds has high affinity and selectivity for GABA A α5 receptor binding sites and might be useful as a cognitive enhancer or for the treatment of cognitive disorders like Alzheimer's disease. The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-7, preferably from 1-4, carbon atoms, for example, methyl, ethyl, propyl, isopropyl, n-butyl, i-butyl, t-butyl and the like.

The term "lower alkynyl" denotes a straight- or branched-chain hydrocarbon group containing from 2-7, preferably from 2-4, carbon atoms, and comprising one, two or three triple bonds, for example, methynyl, ethynyl, propynyl, especially prop-2-ynyl, isopropynyl, n-butynyl, i-butynyl, t-butynyl and the like.

The term "lower alkoxy" denotes a lower alkyl group as defined hereinabove, which is linked via an oxygen atom. Examples of lower alkoxy groups are methoxy and ethoxy.

The term "aryl" denotes an unsaturated aromatic carbon ring, for example a phenyl, benzyl or naphthyl group. A preferred aryl group is phenyl.

The term "halogen" denotes chlorine, iodine, fluorine and bromine.

The term "cycloalkyl" denotes a cyclic hydrocarbon ring, having from 3 to 7 carbon ring atoms, for example, cyclopropyl, cyclopentyl or cyclohexyl.

The term "heterocycloalkyl" denotes a saturated 5 or 6 membered saturated heterocyclic ring containing from one to three heteroatoms, such as N, O or S atoms. Examples of such heterocycloalkyl groups are morpholinyl, azetidin, pyrrolidin, or tetrahydropyranyl as well as those groups which are specifically illustrated by the examples hereinafter.

The term "heteroaryl" denotes an aromatic 5 or 6 membered ring containing from one to three heteroatoms, such as N, O or S atoms. Examples of such aromatic heteroaryl groups are pyridinyl, pyrrolyl, triazolyl, isoxazolyl, furanyl, thiophenyl, imidazolyl, oxazolyl or pyrazinyl.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides aryl-isoxazol-4-yl-imidazo[1,2-a]pyridine derivatives of formula I

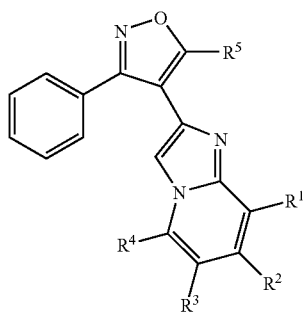

I wherein $R^1$ is hydrogen, halogen, hydroxy, lower alkyl, benzyloxy or —O—(CH$_2$)—(CO)-5 or 6 membered heteroaryl optionally substituted by aryl or by lower alkyl;

$R^2$ is hydrogen, halogen, lower alkyl, lower alkynyl, amino, —NHC(O)—$R^a$ or —(CO)—$R^a$;

$R^3$ is hydrogen, halogen, cyano, lower alkyl, lower alkynyl, amino, —NHC(O)—$R^a$, —(CO)—$R^a$, -5 or 6-membered heterocycloalkyl in the 1-position, optionally substituted by =O or is a -5 or 6-membered heteroaryl in the 1-position;

$R^4$ is hydrogen or -5 or 6-membered heteroaryl;

$R^5$ is lower alkyl or cycloalkyl;

$R^a$ is lower alkoxy or NR'R", wherein R' and R" are each independently hydrogen, lower alkyl optionally substituted by hydroxy, lower alkynyl, —(CH$_2$)$_n$-cycloalkyl, —(CH$_2$)$_n$-5 or 6-membered heterocycloalkyl or —(CH$_2$)$_n$-5 or 6-membered heteroaryl; and n is 0 to 3;

and pharmaceutically acceptable acid addition salts thereof.

Preferred are compounds that have a binding activity (hKi) of lower than 100 nM, are selective for GABA A α5 subunits, and are relatively free of activity at GABA A α1, α2 and α3 receptor binding sites. Most preferred are compounds which have a binding activity (hKi) of lower than 35 nM.

As mentioned hereinabove, the compounds of the invention are those compounds of formula I wherein:

$R^1$ is hydrogen, halogen (preferably Cl or Br), hydroxy, lower alkyl (preferably methyl), benzyloxy or —O—(CH$_2$)—(CO)-5 or 6 membered heteroaryl (preferably izoxazolyl) optionally substituted by aryl (preferably phenyl) or by lower alkyl (preferably methyl);

$R^2$ is hydrogen, halogen (preferably bromo), lower alkyl (preferably methyl or ethyl), lower alkynyl, amino, —NHC(O)—$R^a$ or —(CO)—$R^a$;

$R^3$ is hydrogen, halogen (preferably Cl, F or Br), cyano, lower alkyl (preferably methyl or ethyl), lower alkynyl, amino, —NHC(O)—$R^a$, —(CO)—$R^a$, -5 or 6-membered heterocycloalkyl in the 1-position (preferably azetidin-1-yl, pyrrolidin-1yl), optionally substituted by =O or a -5 or 6-membered heteroaryl in the 1-position, such as imidazolyl or pyrazolyl;

$R^a$ is lower alkoxy (preferably methoxy or ethoxy), NR'R", wherein R' and R" are each independently hydrogen, lower alkyl optionally substituted by hydroxy (preferably hydroxyethyl), lower alkynyl (preferably methynyl or eth-2-ynyl, prop-2-ynyl), —(CH$_2$)$_n$-cycloalkyl (preferably cyclopropyl, methylcyclopropyl, cyclobutyl or cyclopentyl), —(CH$_2$)$_n$-5 or 6-membered heterocycloalkyl (preferably isoxazolyl, morpholinyl, ethylmorpholinyl, propylmorpholinyl or tetrahydropyranyl) or —(CH$_2$)$_n$-5 or 6-membered heteroaryl (preferably pyridinyl or furanyl); and n is 0, 1, 2 or 3.

and pharmaceutically acceptable acid addition salts thereof.

Independently of all the embodiments described in the specification, whenever $R^a$ is —(CH$_2$)$_n$-cycloalkyl, —(CH$_2$)$_n$-5 or 6-membered heterocycloalkyl or —(CH$_2$)$_n$-5 or 6-membered heteroaryl, n is preferably 0 or 1, i.e. preferably cycloalkyl, —CH$_2$-cycloalkyl, 5 or 6-membered heterocycloalkyl, —CH$_2$-5 or 6-membered heterocycloalkyl, 5 or 6-membered heteroaryl, or —CH$_2$-5 or 6-membered heteroaryl.

In a certain embodiment of the compounds of formula I of the invention $R^3$ is hydrogen, for example the following compounds:

2-(5-methyl-3-phenyl-isoxazol-4-yl)-imidazo[1,2-a]pyridine;

8-methyl-2-(5-methyl-3-phenyl-isoxazol-4-yl)-imidazo[1,2-a]pyridine;

8-chloro-2-(5-methyl-3-phenyl-isoxazol-4-yl)-imidazo[1,2-a]pyridine;

8-bromo-2-(5-methyl-3-phenyl-isoxazol-4-yl)-imidazo[1,2-a]pyridine;

2-(5-methyl-3-phenyl-isoxazol-4-yl)-imidazo[1,2-a]pyridin-8-ol 8-benzyloxy-2-(5-methyl-3-phenyl-isoxazol-4-yl)-imidazo[1,2-a]pyridine;

1-(5-methyl-3-phenyl-isoxazol-4-yl)-2-[2-(5-methyl-3-phenyl-isoxazol-4-yl)-imidazo[1,2-a]pyridin-8-yloxy]-ethanone;

7-methyl-2-(5-methyl-3-phenyl-isoxazol-4-yl)-imidazo[1,2-a]pyridine;

7-ethyl-2-(5-methyl-3-phenyl-isoxazol-4-yl)-imidazo[1,2-a]pyridine;

2-(5-methyl-3-phenyl-isoxazol-4-yl)-imidazo[1,2-a]pyridine-7-carboxylic acid methyl ester;
2-(5-methyl-3-phenyl-isoxazol-4-yl)-imidazo[1,2-a]pyridine-7-carboxylic acid cyclopropylmethyl-amide;
2-(5-methyl-3-phenyl-isoxazol-4-yl)-imidazo[1,2-a]pyridine-7-carboxylic acid prop-2-ynylamide;
2-(5-methyl-3-phenyl-isoxazol-4-yl)-imidazo[1,2-a]pyridine-7-carboxylic acid cyclopropylamide;
2-(5-methyl-3-phenyl-isoxazol-4-yl)-imidazo[1,2-a]pyridine-7-carboxylic acid cyclobutylamide;
2-(5-methyl-3-phenyl-isoxazol-4-yl)-imidazo[1,2-a]pyridine-7-carboxylic acid cyclopentylamide;
2-(5-methyl-3-phenyl-isoxazol-4-yl)-imidazo[1,2-a]pyridine-7-carboxylic acid (2-hydroxy-ethyl)-amide;
2-(5-methyl-3-phenyl-isoxazol-4-yl)-imidazo[1,2-a]pyridine-7-carboxylic acid (tetrahydro-pyran-4-yl)-amide;
2-(5-methyl-3-phenyl-isoxazol-4-yl)-imidazo[1,2-a]pyridine-7-carboxylic acid (2-morpholin-4-yl-ethyl)-amide;
2-(5-methyl-3-phenyl-isoxazol-4-yl)-imidazo[1,2-a]pyridine-7-carboxylic acid (3-morpholin-4-yl-propyl)-amide;
2-(5-methyl-3-phenyl-isoxazol-4-yl)-imidazo[1,2-a]pyridine-7-carboxylic acid (pyridin-2-ylmethyl)-amide;
2-(5-methyl-3-phenyl-isoxazol-4-yl)-imidazo[1,2-a]pyridine-7-carboxylic acid (pyridin-3-ylmethyl)-amide;
2-(5-methyl-3-phenyl-isoxazol-4-yl)-imidazo[1,2-a]pyridine-7-carboxylic acid (pyridin-4-ylmethyl)-amide;
2-(5-methyl-3-phenyl-isoxazol-4-yl)-imidazo[1,2-a]pyridine-7-carboxylic acid (furan-2-ylmethyl)-amide;
7-bromo-2-(5-methyl-3-phenyl-isoxazol-4-yl)-imidazo[1,2-a]pyridine;
7-ethynyl-2-(5-methyl-3-phenyl-isoxazol-4-yl)-imidazo[1,2-a]pyridine;
2-(5-methyl-3-phenyl-isoxazol-4-yl)-imidazo[1,2-a]pyridin-7-ylamine;
N-[2-(5-methyl-3-phenyl-isoxazol-4-yl)-imidazo[1,2-a]pyridin-7-yl]-2-pyridin-3-yl-acetamide;
cyclopropanecarboxylic acid [2-(5-methyl-3-phenyl-isoxazol-4-yl)-imidazo[1,2-a]pyridin-7-yl]-amide;
cyclobutanecarboxylic acid [2-(5-methyl-3-phenyl-isoxazol-4-yl)-imidazo[1,2-a]pyridin-7-yl]-amide;
cyclopentanecarboxylic acid [2-(5-methyl-3-phenyl-isoxazol-4-yl)-imidazo[1,2-a]pyridin-7-yl]-amide or
N-[2-(5-methyl-3-phenyl-isoxazol-4-yl)-imidazo[1,2-a]pyridin-7-yl]-nicotinamide;

In a certain embodiment of the compounds of formula I of the invention $R^3$ is halogen, for example the following compounds:
6-fluoro-2-(5-methyl-3-phenyl-isoxazol-4-yl)-imidazo[1,2-a]pyridine;
6-chloro-2-(5-methyl-3-phenyl-isoxazol-4-yl)-imidazo[1,2-a]pyridine;
6-bromo-2-(5-methyl-3-phenyl-isoxazol-4-yl)-imidazo[1,2-a]pyridine;
6-Iodo-2-(5-methyl-3-phenyl-isoxazol-4-yl)-imidazo[1,2-a]pyridine and
6-bromo-2-(5-cyclopropyl-3-phenyl-isoxazol-4-yl)-imidazo[1,2-a]pyridine.

In a certain embodiment of the compounds of formula I of the invention $R^3$ is cyano, for example 2-(5-methyl-3-phenyl-isoxazol-4-yl)-imidazo[1,2-a]pyridine-6-carbonitrile.

In a certain embodiment of the compounds of formula I of the invention $R^3$ is lower alkyl, for example 6-methyl-2-(5-methyl-3-phenyl-isoxazol-4-yl)-imidazo[1,2-a]pyridine.

In a certain embodiment of the compounds of formula I of the invention $R^3$ is —C(O)—$R^a$, wherein $R^a$ is lower alkoxy or NR'R'', wherein R' and R'' are each independently hydrogen, lower alkyl optionally substituted by hydroxy, lower alkynyl, —(CH$_2$)$_n$-cycloalkyl, —(CH$_2$)$_n$-5 or 6-membered heterocycloalkyl or —(CH$_2$)$_n$-5 or 6-membered heteroaryl; and n is 0 to 3, for example the following compounds:
2-(5-methyl-3-phenyl-isoxazol-4-yl)-imidazo[1,2-a]pyridine-6-carboxylic acid methyl ester;
2-(5-methyl-3-phenyl-isoxazol-4-yl)-imidazo[1,2-a]pyridine-6-carboxylic acid ethyl ester;
2-(5-methyl-3-phenyl-isoxazol-4-yl)-imidazo[1,2-a]pyridine-6-carboxylic acid cyclopropylmethyl-amide;
2-(5-methyl-3-phenyl-isoxazol-4-yl)-imidazo[1,2-a]pyridine-6-carboxylic acid prop-2-ynylamide;
2-(5-methyl-3-phenyl-isoxazol-4-yl)-imidazo[1,2-a]pyridine-6-carboxylic acid cyclopropylamide;
2-(5-methyl-3-phenyl-isoxazol-4-yl)-imidazo[1,2-a]pyridine-6-carboxylic acid cyclobutylamide;
2-(5-methyl-3-phenyl-isoxazol-4-yl)-imidazo[1,2-a]pyridine-6-carboxylic acid cyclopentylamide;
2-(5-methyl-3-phenyl-isoxazol-4-yl)-imidazo[1,2-a]pyridine-6-carboxylic acid (2-hydroxy-ethyl)-amide;
2-(5-methyl-3-phenyl-isoxazol-4-yl)-imidazo[1,2-a]pyridine-6-carboxylic acid (tetrahydro-pyran-4-yl)-amide;
2-(5-methyl-3-phenyl-isoxazol-4-yl)-imidazo[1,2-a]pyridine-6-carboxylic acid (2-morpholin-4-yl-ethyl)-amide;
2-(5-methyl-3-phenyl-isoxazol-4-yl)-imidazo[1,2-a]pyridine-6-carboxylic acid (3-morpholin-4-yl-propyl)-amide;
2-(5-methyl-3-phenyl-isoxazol-4-yl)-imidazo[1,2-a]pyridine-6-carboxylic acid (pyridin-2-ylmethyl)-amide;
2-(5-methyl-3-phenyl-isoxazol-4-yl)-imidazo[1,2-a]pyridine-6-carboxylic acid (pyridin-3-ylmethyl)-amide;
2-(5-methyl-3-phenyl-isoxazol-4-yl)-imidazo[1,2-a]pyridine-6-carboxylic acid (pyridin-4-ylmethyl)-amide; and
2-(5-methyl-3-phenyl-isoxazol-4-yl)-imidazo[1,2-a]pyridine-6-carboxylic acid (furan-2-ylmethyl)-amide.

In a certain embodiment of the compounds of formula I of the invention $R^3$ is amino, —NHC(O)—$R^a$, -5 or 6-membered heterocycloalkyl in the 1-position, optionally substituted by =O or -5 or 6-membered heteroaryl in the 1-position, for example the following compounds:
2-(5-methyl-3-phenyl-isoxazol-4-yl)-imidazo[1,2-a]pyridin-6-ylamine;
2-cyclopropyl-N-[2-(5-methyl-3-phenyl-isoxazol-4-yl)-imidazo[1,2-a]pyridin-6-yl]-acetamide;
N-[2-(5-methyl-3-phenyl-isoxazol-4-yl)-imidazo[1,2-a]pyridin-6-yl]-2-pyridin-3-yl-acetamide;
cyclopropanecarboxylic acid [2-(5-methyl-3-phenyl-isoxazol-4-yl)-imidazo[1,2-a]pyridin-6-yl]-amide;
cyclobutanecarboxylic acid [2-(5-methyl-3-phenyl-isoxazol-4-yl)-imidazo[1,2-a]pyridin-6-yl]-amide;
cyclopentanecarboxylic acid [2-(5-methyl-3-phenyl-isoxazol-4-yl)-imidazo[1,2-a]pyridin-6-yl]-amide;
N-[2-(5-methyl-3-phenyl-isoxazol-4-yl)-imidazo[1,2-a]pyridin-6-yl]-benzamide;
N-[2-(5-methyl-3-phenyl-isoxazol-4-yl)-imidazo[1,2-a]pyridin-6-yl]-nicotinamide;

1-[2-(5-methyl-3-phenyl-isoxazol-4-yl)-imidazo[1,2-a]pyridin-6-yl]-azetidin-2-one;

1-[2-(5-methyl-3-phenyl-isoxazol-4-yl)-imidazo[1,2-a]pyridin-6-yl]-pyrrolidin-2-one;

2-(5-methyl-3-phenyl-isoxazol-4-yl)-6-pyrrol-1-yl-imidazo[1,2-a]pyridine;

2-(5-methyl-3-phenyl-isoxazol-4-yl)-6-pyrazol-1-yl-imidazo[1,2-a]pyridine and 6-imidazol-1-yl-2-(5-methyl-3-phenyl-isoxazol-4-yl)-imidazo[1,2-a]pyridine.

The present compounds of formula I and their pharmaceutically acceptable salts can be prepared by methods known in the art, for example, by processes described below, which process comprises:

reacting a compound of formula

II with a compound of formula:

III to give a compound of formula:

I wherein R¹, R², R³, R⁴ and R⁵ are as described above, and, if desired, converting a compound of formula I into a pharmaceutically acceptable salt. The process described above allows the preparation of all the compounds encompassed by the invention.

The following scheme describes the processes for preparation of certain compounds of formula I in more detail.

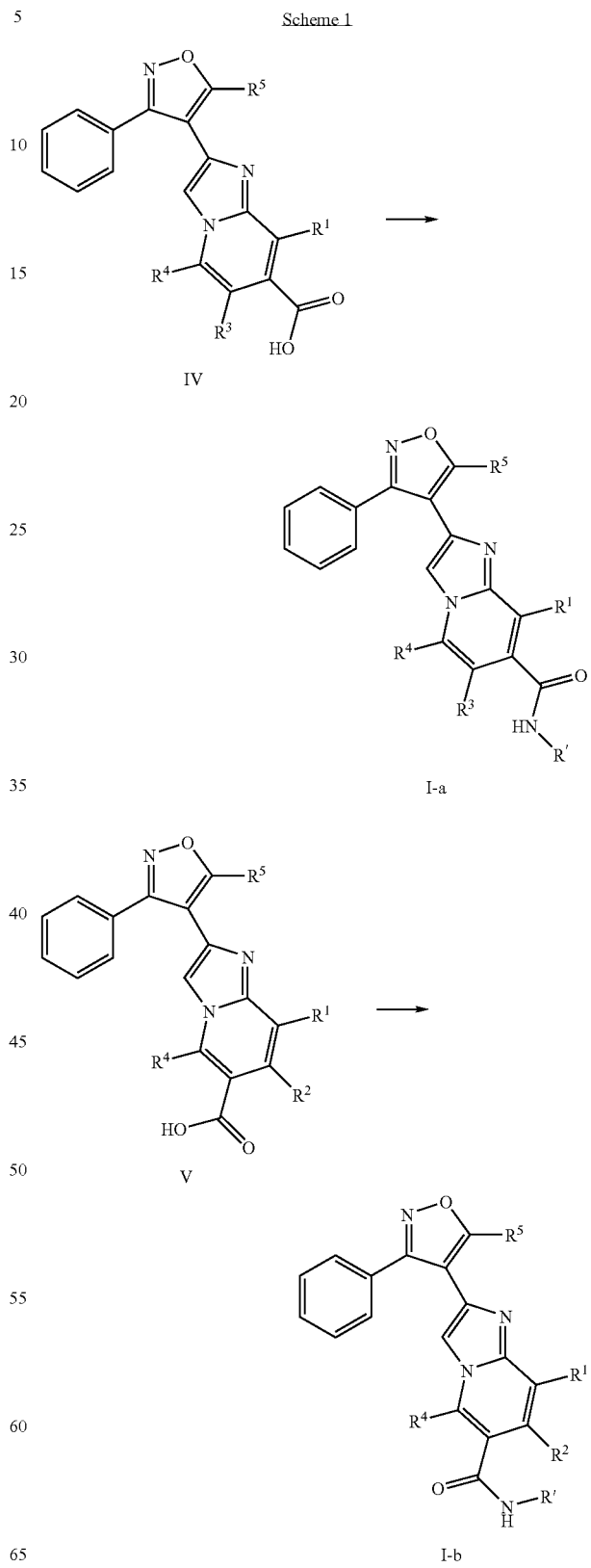

In accordance with Scheme 1, the acids of formula IV or V can be treated with standard amide bond coupling methods, such as treatment with TBTU in a suitable solvent, such as DMF, followed by the addition of a suitable base, such as diisopropylethylamine, followed by the addition of the appropriate amine to give the compounds of formulae I-a or I-b. The compound of formula I-a is a compound of formula I, wherein $R^2$ is —(CO)—$R^a$ with $R^a$ is NR'R" wherein R" is hydrogen and R' is as defined hereinabove. The compound of formula I-b is a compound of formula I, wherein $R^3$ is —(CO)—$R^a$ with $R^a$ is NR'R" wherein R" is hydrogen and R' is as defined herein above.

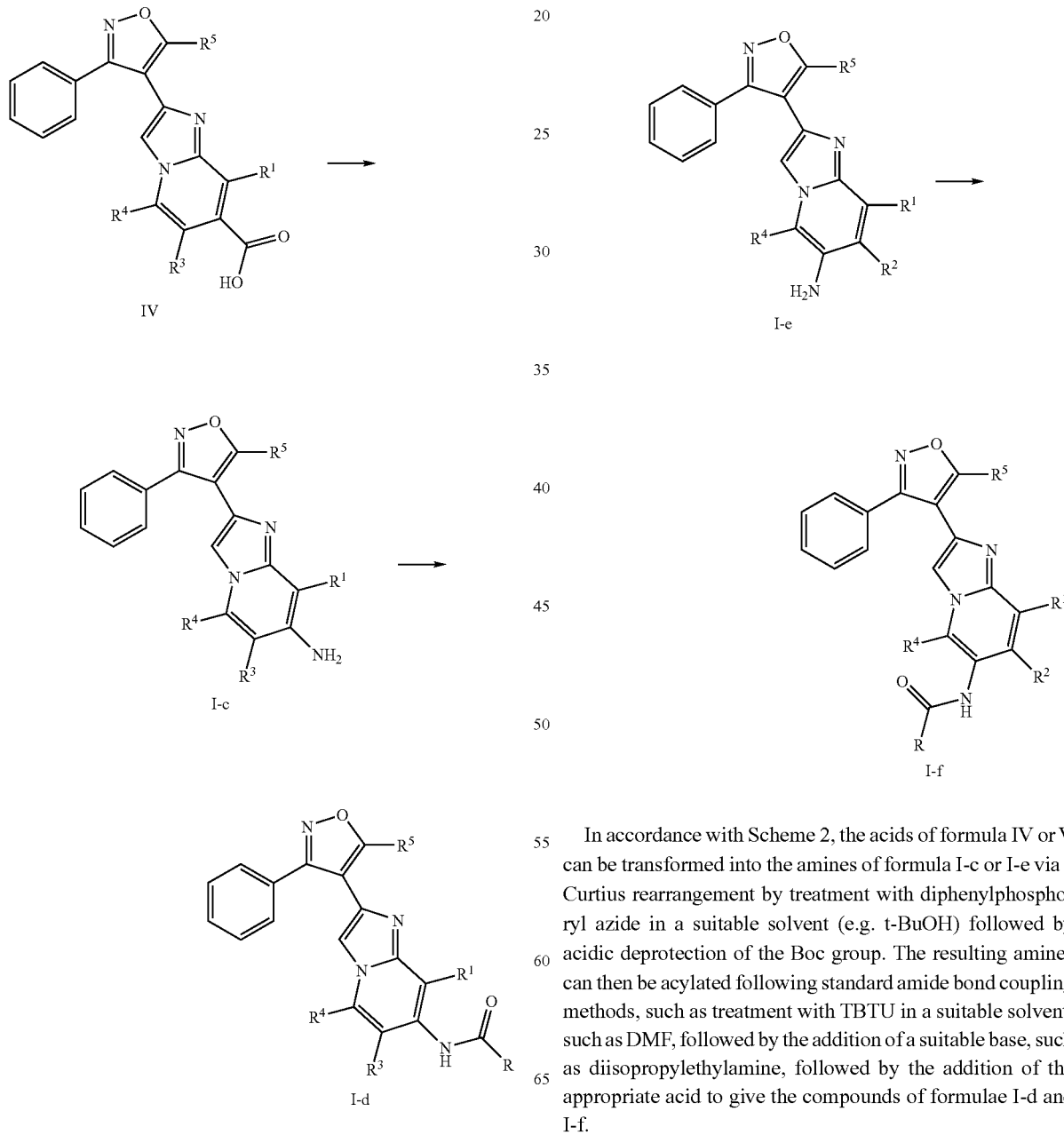

In accordance with Scheme 2, the acids of formula IV or V can be transformed into the amines of formula I-c or I-e via a Curtius rearrangement by treatment with diphenylphosphoryl azide in a suitable solvent (e.g. t-BuOH) followed by acidic deprotection of the Boc group. The resulting amines can then be acylated following standard amide bond coupling methods, such as treatment with TBTU in a suitable solvent, such as DMF, followed by the addition of a suitable base, such as diisopropylethylamine, followed by the addition of the appropriate acid to give the compounds of formulae I-d and I-f.

Scheme 3

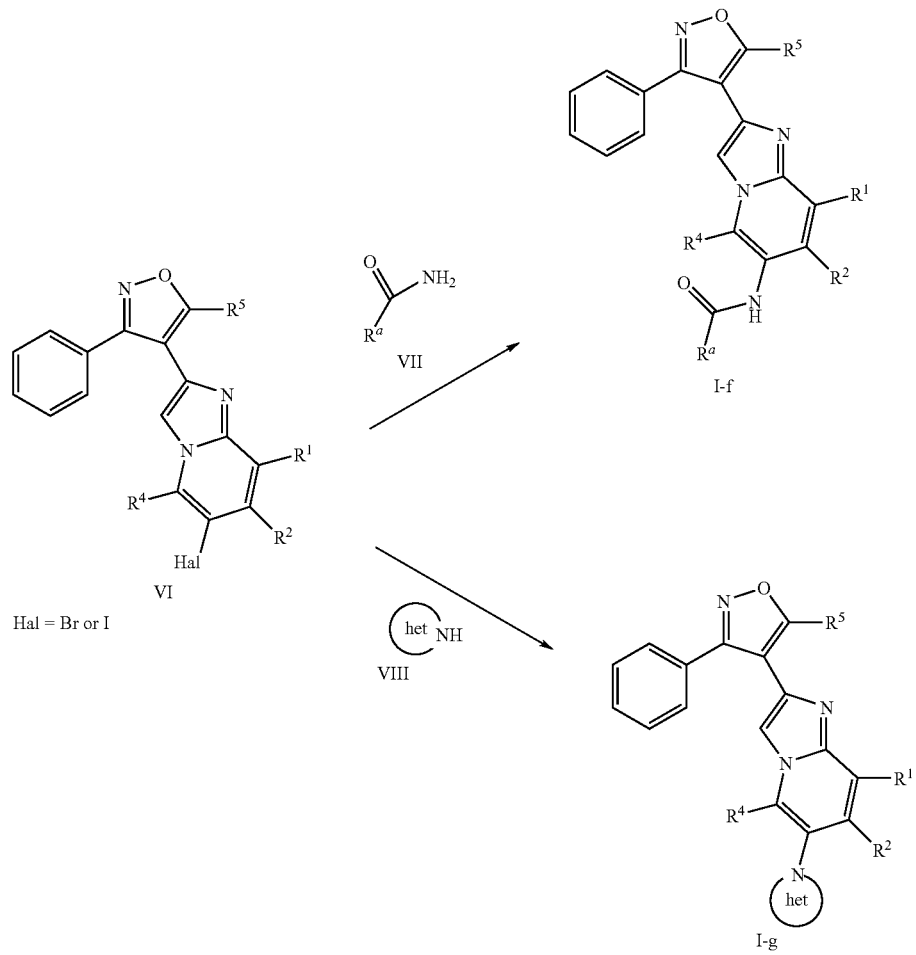

In accordance with Scheme 3, the halogenated compounds of formula VI can be transformed into the products of formula I-f and I-g via standard copper catalysed N-aryl bond formation such as treatment of an amide of formula VII or N-containing 5- or 6-membered heterocyclyl or heteroaryl compound of formula VIII in the presence of cesium carbonate in a suitable solvent such as DMF in the presence of a copper source such as CuI followed by heating in a microwave oven at elevated temperatures such as 200° C.

As mentioned earlier, the compounds of formula I and their pharmaceutically usable salts possess valuable pharmacological properties. It has been found that the compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition $\alpha1\beta3\gamma2$, $\alpha2\beta3\gamma2$, $\alpha3\beta3\gamma2$ and $\alpha5\beta3\gamma2$.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer 50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from α5 subunits of the rat GABA A receptor of 300 nM or less. In a preferred embodiment the compounds of the invention are binding selective for the α5 subunit relative to the α1, α2 and α3 subunit.

| Example No. | Ki[nM]hα5 |
| --- | --- |
| 1 | 166.8 |
| 2 | 231.7 |
| 3 | 126.4 |
| 4 | 146.1 |
| 5 | 20.2 |
| 6 | 23.0 |
| 7 | 125.8 |
| 8 | 81.7 |
| 9 | 101.2 |
| 10 | 149.6 |
| 11 | 177.7 |
| 12 | 72.3 |
| 13 | 87.4 |
| 14 | 168.5 |
| 15 | 200 |
| 16 | 114.3 |
| 17 | 96.0 |
| 18 | 159.1 |
| 19 | 124.3 |
| 21 | 97 |
| 22 | 198.7 |
| 23 | 182.8 |
| 24 | 33.1 |
| 25 | 154.4 |
| 26 | 109.6 |
| 27 | 120.9 |
| 28 | 172.7 |
| 29 | 116.9 |
| 30 | 154.4 |
| 31 | 23.9 |
| 32 | 44.5 |
| 33 | 23.6 |
| 34 | 19.8 |
| 35 | 15.8 |
| 36 | 59.8 |
| 37 | 6.8 |
| 38 | 174.2 |
| 39 | 190 |
| 41 | 41.2 |
| 42 | 85.5 |
| 43 | 36.9 |
| 44 | — |
| 45 | 189.5 |
| 46 | 90.3 |
| 47 | 50.7 |
| 48 | 79.4 |
| 49 | 80.5 |
| 50 | 85.9 |
| 51 | 76.2 |
| 52 | 143.4 |
| 53 | 164.2 |
| 54 | 88.1 |
| 55 | 38.4 |
| 56 | 54.3 |
| 57 | 20.8 |
| 58 | 28.2 |
| 59 | 54.7 |
| 60 | 30.7 |
| 61 | 9.4 |
| 62 | 27.0 |
| 63 | 48.7 |
| 64 | 73.2 |
| 65 | 41.1 |
| 66 | 57.4 |
| 67 | 13.4 |
| 68 | 5.5 |
| 69 | 7.13 |

The invention also provides pharmaceutical compositions containing compounds of the invention, for example compounds of formula I and/or their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acid or its salts etc can be used as such excipients e.g. for tablets, dragées and hard gelatine capsules. Suitable excipients for soft gelatine capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions of the invention can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of the invention and, if desired, one or more other therapeutically valuable substances into a galenical administration form together with one or more therapeutically inert carriers.

Compounds of the invention have high affinity and selectivity for GABA A α5 receptor binding sites. The invention provides a method for enhancing cognition which comprises administering to an individual a therapeutically effective amount of a compound of formula I or a pharmaceutically acceptable salt thereof. Further, the invention provides a method for the treatment of Alzheimer's disease which comprises administering to an individual a therapeutically effective amount of a compound of formula I or a pharmaceutically acceptable salt thereof.

The compounds and compositions of the invention can be administered in a conventional manner, for example, orally, rectally, or parenterally. The compounds of the invention can be administered orally, for example, in the form of tablets, coated tablets, dragées, hard and soft gelatin capsules, solutions, emulsions, or suspensions. The compounds of the invention also can be administered rectally, for example, in the form of suppositories, or parenterally, for example, in the form of injectable solutions.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1-69 are provided for illustration of the invention. They should not be considered as limiting the scope of the invention, but merely as being representative thereof.

EXAMPLE 1

2-(5-Methyl-3-phenyl-isoxazol-4-yl)-imidazo[1,2-a]pyridine

A mixture of 4-(bromoacetyl)-5-methyl-3-phenylisoxazole (commercially available) (140 mg, 0.5 mmol) and 2-aminopyridine (47 mg, 0.5 mmol) in ethanol (3.1 mL) was heated under reflux under argon for 3.5 h. Then another portion of 2-aminopyridine (24 mg, 0.25 mmol) was added and heating under reflux continued for another 1 h. The resulting mixture was then cooled to room temperature and then sodium hydrogen carbonate (63 mg, 0.75 mmol) added and the resulting mixture heated under reflux for 2 h. After cooling to room temperature, the mixture was poured onto water and extracted with ethyl acetate. The combined organic layers were then washed with water and brine, dried over sodium sulphate and evaporated to leave a yellow oil. Purification by chromatography ($SiO_2$, heptane:ethyl acetate=100:0 to 50:50) afforded the title compound (76 mg, 55%) which was obtained as a light yellow gum. MS: m/e=276.0 $[M+H]^+$.

EXAMPLE 2

8-Methyl-2-(5-methyl-3-phenyl-isoxazol-4-yl)-imidazo[1,2-a]pyridine

A mixture of 4-(bromoacetyl)-5-methyl-3-phenylisoxazole (commercially available) (112 mg, 0.4 mmol) and 2-amino-3-methylpyridine (43 mg, 0.4 mmol) in ethanol (2.5 mL) was heated under reflux under argon for 5 h. The mixture was then poured onto water and extracted with ethyl acetate. The combined organic layers were then washed with water and brine, dried over sodium sulphate and evaporated to leave a yellow oil. Purification by chromatography ($SiO_2$, heptane:ethyl acetate=100:0 to 25:75) afforded the title compound (46 mg, 40%) which was obtained as a colourless oil. MS: m/e=290.3 $[M+H]^+$.

EXAMPLE 3

8-Chloro-2-(5-methyl-3-phenyl-isoxazol-4-yl)-imidazo[1,2-a]pyridine

As described for Example 1, 4-(bromoacetyl)-5-methyl-3-phenylisoxazole (commercially available) (140 mg, 0.5 mmol) was converted, using 2-amino-3-chloropyridine instead of 2-aminopyridine, to the title compound (117 mg, 76%) which was obtained as a yellow foam. MS: m/e=310.3 $[M+H]^+$.

EXAMPLE 4

8-Bromo-2-(5-methyl-3-phenyl-isoxazol-4-yl)-imidazo[1,2-a]pyridine

As described for Example 1, 4-(bromoacetyl)-5-methyl-3-phenylisoxazole (commercially available) (140 mg, 0.5 mmol) was converted, using 2-amino-3-bromopyridine instead of 2-aminopyridine, to the title compound (85 mg, 48%) which was obtained as a yellow gum. MS: m/e=354.0/356.1 $[M+H]^+$.

EXAMPLE 5

2-(5-Methyl-3-phenyl-isoxazol-4-yl)-imidazo[1,2-a]pyridin-8-ol

As described for Example 2, 4-(bromoacetyl)-5-methyl-3-phenylisoxazole (commercially available) (140 mg, 0.5 mmol) was converted, using 2-amino-3-hydroxypyridine instead of 2-amino-3-methylpyridine, to the title compound (6 mg, 4%) which was obtained as a yellow foam. MS: m/e=292.1 [M+H]$^+$.

EXAMPLE 6

8-Benzyloxy-2-(5-methyl-3-phenyl-isoxazol-4-yl)-imidazo[1,2-a]pyridine

As described for Example 2, 4-(bromoacetyl)-5-methyl-3-phenylisoxazole (commercially available) (140 mg, 0.5 mmol) was converted, using 2-amino-3-benzyloxypyridine instead of 2-amino-3-methylpyridine, to the title compound (96 mg, 50%) which was obtained as a light yellow solid. MS: m/e=382.3 [M+H]$^+$.

EXAMPLE 7

1-(5-Methyl-3-phenyl-isoxazol-4-yl)-2-[2-(5-methyl-3-phenyl-isoxazol-4-yl)-imidazo[1,2-a]pyridin-8-yloxy]-ethanone As described for Example 2, 4-(bromoacetyl)-5-methyl-3-phenylisoxazole (commercially available) (140 mg, 0.5 mmol) was converted, using 2-amino-3-hydroxypyridine instead of 2-amino-3-methylpyridine, to the title compound (18 mg, 7%) which was obtained as a yellow foam. MS: m/e=491.3 [M+H]$^+$.

EXAMPLE 8

7-Methyl-2-(5-methyl-3-phenyl-isoxazol-4-yl)-imidazo[1,2-a]pyridine

As described for Example 2, 4-(bromoacetyl)-5-methyl-3-phenylisoxazole (commercially available) (140 mg, 0.5 mmol) was converted, using 2-amino-4-methylpyridine instead of 2-amino-3-methylpyridine, to the title compound (22 mg, 19%) which was obtained as a yellow solid. MS: m/e=290.0 [M+H]$^+$.

EXAMPLE 9

7-Ethyl-2-(5-methyl-3-phenyl-isoxazol-4-yl)-imidazo[1,2-a]pyridine

As described for Example 2, 4-(bromoacetyl)-5-methyl-3-phenylisoxazole (commercially available) (140 mg, 0.5 mmol) was converted, using 2-amino-4-ethylpyridine instead of 2-amino-3-methylpyridine, to the title compound (33 mg, 27%) which was obtained as a yellow oil. MS: m/e=304.0 [M+H]$^+$.

EXAMPLE 10

2-(5-Methyl-3-phenyl-isoxazol-4-yl)-imidazo[1,2-a]pyridine-7-carboxylic acid methyl ester As described for Example 1, 4-(bromoacetyl)-5-methyl-3-phenylisoxazole (commercially available) (280 mg, 1.0 mmol) was converted, using methyl 2-aminopyridine-4-carboxylate instead of 2-aminopyridine, to the title compound (194 mg, 58%) which was obtained as a yellow foam. MS: m/e=334.1 [M+H]$^+$.

EXAMPLE 11

2-(5-Methyl-3-phenyl-isoxazol-4-yl)-imidazo[1,2-a]pyridine-7-carboxylic acid cyclopropylmethyl-amide a) 2-(5-Methyl-3-phenyl-isoxazol-4-yl)-imidazo[1,2-a]pyridine-7-carboxylic acid To a solution of 2-(5-methyl-3-phenyl-isoxazol-4-yl)-imidazo[1,2-a]pyridine-7-carboxylic acid methyl ester (1.2 g, 3.6 mmol) in THF (9.9 mL), water (9.9 mL) and methanol (2.2 mL) was added lithium hydroxide monohydrate (302 mg, 7.2 mmol) and the resulting mixture stirred vigorously overnight. The mixture was then evaporated and acidified with hydrochloric acid (1 N) and then extracted with ethyl acetate. The combined organic layers were then washed with water and brine, dried over sodium sulphate and evaporated to leave a yellow solid. Purification by trituration with heptane afforded the title compound (764 mg, 66%) which was obtained as a yellow solid. MS: m/e=318.1 [M−H]$^-$.

b) 2-(5-Methyl-3-phenyl-isoxazol-4-yl)-imidazo[1,2-a]pyridine-7-carboxylic acid cyclopropylmethyl-amide To a solution of 2-(5-methyl-3-phenyl-isoxazol-4-yl)-imidazo[1,2-a]pyridine-7-carboxylic acid (64 mg, 0.2 mmol) in DMF (0.3 mL) was added N,N,N',N'-tetramethyl-O-(benzotriazol-1-yl)uranium tetrafluoroborate (71 mg, 0.22 mmol), N,N-diisopropyl ethyl amine (129 mg, 1.0 mmol) and aminomethylcyclopropane (19 μL, 0.22 mmol) and the resulting mixture stirred at room temperature for 1 h. The resulting mixture was then poured into a mixture of brine:water (1:1) and extracted with ethyl acetate. The combined organic layers were then washed with brine, dried over sodium sulphate and evaporated to leave a yellow oil. Purification by chromatography (SiO$_2$, heptane:ethyl acetate=100:0 to 25:75) afforded the title compound (55 mg, 74%) which was obtained as a yellow solid. MS: m/e=373.1 [M+H]$^+$.

EXAMPLE 12

2-(5-Methyl-3-phenyl-isoxazol-4-yl)-imidazo[1,2-a]pyridine-7-carboxylic acid prop-2-ynylamide As described for Example 11b, 2-(5-methyl-3-phenyl-isoxazol-4-yl)-imidazo[1,2-a]pyridine-7-carboxylic acid (64 mg, 0.2 mmol) was converted, using propargylamine instead of aminomethylcyclopropane, to the title compound (45 mg, 63%) which was obtained as a white solid. MS: m/e=357.1 [M+H]$^+$.

EXAMPLE 13

2-(5-Methyl-3-phenyl-isoxazol-4-yl)-imidazo[1,2-a]pyridine-7-carboxylic acid cyclopropylamide As described for Example 11b, 2-(5-methyl-3-phenyl-isoxazol-4-yl)-imidazo[1,2-a]pyridine-7-carboxylic acid (64 mg, 0.2 mmol) was converted, using cyclopropylamine instead of aminomethylcyclopropane, to the title compound (35 mg, 48%) which was obtained as a yellow solid. MS: m/e=359.3 [M+H]$^+$.

EXAMPLE 14

2-(5-Methyl-3-phenyl-isoxazol-4-yl)-imidazo[1,2-a]pyridine-7-carboxylic acid cyclobutylamide As described for Example 11b, 2-(5-methyl-3-phenyl-isoxazol-4-yl)-imidazo[1,2-a]pyridine-7-carboxylic acid (96 mg, 0.3 mmol) was converted, using cyclobutylamine instead of aminomethylcyclopropane, to the title compound (89 mg, 80%) which was obtained as a light yellow foam. MS: m/e=373.0 [M+H]$^+$.

EXAMPLE 15

2-(5-Methyl-3-phenyl-isoxazol-4-yl)-imidazo[1,2-a]pyridine-7-carboxylic acid cyclopentylamide As described for Example 11b, 2-(5-methyl-3-phenyl-isoxazol-4-yl)-imidazo[1,2-a]pyridine-7-carboxylic acid (96 mg, 0.3 mmol) was converted, using cyclopentylamine instead of aminomethylcyclopropane, to the title compound (84 mg, 73%) which was obtained as a light yellow foam. MS: m/e=387.3 [M+H]$^+$.

EXAMPLE 16

2-(5-Methyl-3-phenyl-isoxazol-4-yl)-imidazo[1,2-a]pyridine-7-carboxylic acid (2-hydroxy-ethyl)-amide As described for Example 11b, 2-(5-methyl-3-phenyl-isoxazol-4-yl)-imidazo[1,2-a]pyridine-7-carboxylic acid (96 mg, 0.3 mmol) was converted, using ethanolamine instead of aminomethylcyclopropane, to the title compound (78 mg, 72%) which was obtained as a light yellow foam. MS: m/e=363.3 [M+H]$^+$.

EXAMPLE 17

2-(5-Methyl-3-phenyl-isoxazol-4-yl)-imidazo[1,2-a]pyridine-7-carboxylic acid (tetrahydro-pyran-4-yl)-amide As described for Example 11b, 2-(5-methyl-3-phenyl-isoxazol-4-yl)-imidazo[1,2-a]pyridine-7-carboxylic acid (85 mg, 0.27 mmol) was converted, using 4-aminotetrahydropyran instead of aminomethylcyclopropane, to the title compound (61 mg, 57%) which was obtained as a yellow solid. MS: m/e=403.5 [M+H]$^+$.

EXAMPLE 18

2-(5-Methyl-3-phenyl-isoxazol-4-yl)-imidazo[1,2-a]pyridine-7-carboxylic acid (2-morpholin-4-yl-ethyl)-amide As described for Example 11b, 2-(5-methyl-3-phenyl-isoxazol-4-yl)-imidazo[1,2-a]pyridine-7-carboxylic acid (64 mg, 0.2 mmol) was converted, using N-(2-aminoethyl)morpholine instead of aminomethylcyclopropane, to the title compound (41 mg, 48%) which was obtained as a light yellow foam. MS: m/e=432.5 [M+H]$^+$.

EXAMPLE 19

2-(5-Methyl-3-phenyl-isoxazol-4-yl)-imidazo[1,2-a]pyridine-7-carboxylic acid (3-morpholin-4-yl-propyl)-amide As described for Example 11b, 2-(5-methyl-3-phenyl-isoxazol-4-yl)-imidazo[1,2-a]pyridine-7-carboxylic acid (96 mg, 0.3 mmol) was converted, using N-(3-aminopropyl)morpholine instead of aminomethylcyclopropane, to the title compound (102 mg, 76%) which was obtained as an off-white foam. MS: m/e=446.3 [M+H]$^+$.

EXAMPLE 20

2-(5-Methyl-3-phenyl-isoxazol-4-yl)-imidazo[1,2-a]pyridine-7-carboxylic acid (pyridin-2-ylmethyl)-amide As described for Example 11b, 2-(5-methyl-3-phenyl-isoxazol-4-yl)-imidazo[1,2-a]pyridine-7-carboxylic acid (96 mg, 0.3 mmol) was converted, using 2-(aminomethyl)pyridine instead of aminomethylcyclopropane, to the title compound (89 mg, 72%) which was obtained as a yellow foam. MS: m/e=410.3 [M+H]$^+$.

EXAMPLE 21

2-(5-Methyl-3-phenyl-isoxazol-4-yl)-imidazo[1,2-a]pyridine-7-carboxylic acid (pyridin-3-ylmethyl)-amide As described for Example 11b, 2-(5-methyl-3-phenyl-isoxazol-4-yl)-imidazo[1,2-a]pyridine-7-carboxylic acid (64 mg, 0.2 mmol) was converted, using 3-(aminomethyl)pyridine instead of aminomethylcyclopropane, to the title compound (54 mg, 66%) which was obtained as a light yellow foam. MS: m/e=410.3 [M+H]$^+$.

EXAMPLE 22

2-(5-Methyl-3-phenyl-isoxazol-4-yl)-imidazo[1,2-a]pyridine-7-carboxylic acid (pyridin-4-ylmethyl)-amide As described for Example 11b, 2-(5-methyl-3-phenyl-isoxazol-4-yl)-imidazo[1,2-a]pyridine-7-carboxylic acid (96 mg, 0.3 mmol) was converted, using 4-picolylamine instead of aminomethylcyclopropane, to the title compound (95 mg, 77%) which was obtained as a light yellow foam. MS: m/e=410.4 [M+H]$^+$.

EXAMPLE 23

2-(5-Methyl-3-phenyl-isoxazol-4-yl)-imidazo[1,2-a]pyridine-7-carboxylic acid (furan-2-ylmethyl)-amide As described for Example 11b, 2-(5-methyl-3-phenyl-isoxazol-4-yl)-imidazo[1,2-a]pyridine-7-carboxylic acid (64 mg, 0.2 mmol) was converted, using furfurylamine instead of aminomethylcyclopropane, to the title compound (57 mg, 72%) which was obtained as a yellow foam. MS: m/e=399.1 [M+H]$^+$.

EXAMPLE 24

6-Methyl-2-(5-methyl-3-phenyl-isoxazol-4-yl)-imidazo[1,2-a]pyridine

As described for Example 2, 4-(bromoacetyl)-5-methyl-3-phenylisoxazole (commercially available) (112 mg, 0.4 mmol) was converted, using 2-amino-5-methylpyridine instead of 2-amino-3-methylpyridine, to the title compound (24 mg, 21%) which was obtained as a yellow oil. MS: m/e=290.1 $[M+H]^+$.

EXAMPLE 25

6-Fluoro-2-(5-methyl-3-phenyl-isoxazol-4-yl)-imidazo[1,2-a]pyridine

As described for Example 2, 4-(bromoacetyl)-5-methyl-3-phenylisoxazole (commercially available) (112 mg, 0.4 mmol) was converted, using 2-amino-5-fluoropyridine instead of 2-amino-3-methylpyridine, to the title compound (15 mg, 13%) which was obtained as a yellow solid. MS: m/e=294.3 $[M+H]^+$.

EXAMPLE 26

6-Chloro-2-(5-methyl-3-phenyl-isoxazol-4-yl)-imidazo[1,2-a]pyridine

As described for Example 1, 4-(bromoacetyl)-5-methyl-3-phenylisoxazole (commercially available) (140 mg, 0.5 mmol) was converted, using 2-amino-5-chloropyridine instead of 2-aminopyridine, to the title compound (82 mg, 53%) which was obtained as a yellow gum. MS: m/e=310.3 $[M+H]^+$.

EXAMPLE 27

6-Bromo-2-(5-methyl-3-phenyl-isoxazol-4-yl)-imidazo[1,2-a]pyridine

As described for Example 1, 4-(bromoacetyl)-5-methyl-3-phenylisoxazole (commercially available) (140 mg, 0.5 mmol) was converted, using 2-amino-5-bromopyridine instead of 2-aminopyridine, to the title compound (75 mg, 42%) which was obtained as a yellow gum. MS: m/e=354.1/356.0 $[M+H]^+$.

EXAMPLE 28

2-(5-Methyl-3-phenyl-isoxazol-4-yl)-imidazo[1,2-a]pyridine-6-carbonitrile

As described for Example 1, 4-(bromoacetyl)-5-methyl-3-phenylisoxazole (commercially available) (140 mg, 0.5 mmol) was converted, using 2-amino-5-cyanopyridine instead of 2-aminopyridine, to the title compound (17 mg, 11%) which was obtained as a light yellow foam. MS: m/e=301.3 $[M+H]^+$.

EXAMPLE 29

2-(5-Methyl-3-phenyl-isoxazol-4-yl)-imidazo[1,2-a]pyridine-6-carboxylic acid methyl ester As described for Example 1, 4-(bromoacetyl)-5-methyl-3-phenylisoxazole (commercially available) (140 mg, 0.5 mmol) was converted, using methyl 6-aminonicotinate instead of 2-aminopyridine, to the title compound (64 mg, 38%) which was obtained as a light yellow solid. MS: m/e=334.3 $[M+H]^+$.

EXAMPLE 30

2-(5-Methyl-3-phenyl-isoxazol-4-yl)-imidazo[1,2-a]pyridine-6-carboxylic acid ethyl ester As described for Example 1, 4-(bromoacetyl)-5-methyl-3-phenylisoxazole (commercially available) (140 mg, 0.5 mmol) was converted, using methyl 6-aminonicotinate instead of 2-aminopyridine, to the title compound (12 mg, 7%) which was obtained as a light yellow gum. MS: m/e=348.4 $[M+H]^+$.

EXAMPLE 31

2-(5-Methyl-3-phenyl-isoxazol-4-yl)-imidazo[1,2-a]pyridine-6-carboxylic acid cyclopropylmethyl-amide a) 2-(5-Methyl-3-phenyl-isoxazol-4-yl)-imidazo[1,2-a]pyridine-6-carboxylic acid As described for Example 11a, 2-(5-methyl-3-phenyl-isoxazol-4-yl)-imidazo[1,2-a]pyridine-6-carboxylic acid methyl ester (2.0 g, 6.0 mmol), instead of 2-(5-methyl-3-phenyl-isoxazol-4-yl)-imidazo[1,2-a]pyridine-7-carboxylic acid methyl ester, was converted to the title compound (1.7 g, 90%) which was obtained as a yellow solid. MS: m/e=318.4 $[M-H]^-$.

b) 2-(5-Methyl-3-phenyl-isoxazol-4-yl)-imidazo[1,2-a]pyridine-6-carboxylic acid cyclopropylmethyl-amide As described for Example 11b, 2-(5-methyl-3-phenyl-isoxazol-4-yl)-imidazo[1,2-a]pyridine-6-carboxylic acid (64 mg, 0.2 mmol), instead of 2-(5-methyl-3-phenyl-isoxazol-4-yl)-imidazo[1,2-a]pyridine-7-carboxylic acid, was converted to the title compound (61 mg, 82%) which was obtained as a light yellow foam. MS: m/e=373.3 $[M+H]^+$.

EXAMPLE 32

2-(5-Methyl-3-phenyl-isoxazol-4-yl)-imidazo[1,2-a]pyridine-6-carboxylic acid prop-2-ynylamide As described for Example 12, 2-(5-methyl-3-phenyl-isoxazol-4-yl)-imidazo[1,2-a]pyridine-6-carboxylic acid (64 mg, 0.2 mmol), instead of 2-(5-methyl-3-phenyl-isoxazol-4-yl)-imidazo[1,2-a]pyridine-7-carboxylic acid, was converted to the title compound (52 mg, 73%) which was obtained as a white solid. MS: m/e=357.1 $[M+H]^+$.

EXAMPLE 33

2-(5-Methyl-3-phenyl-isoxazol-4-yl)-imidazo[1,2-a]pyridine-6-carboxylic acid cyclopropylamide As described for Example 13, 2-(5-methyl-3-phenyl-isoxazol-4-yl)-imidazo[1,2-a]pyridine-6-carboxylic acid (64 mg, 0.2 mmol), instead of 2-(5-methyl-3-phenyl-isoxazol-4-yl)-imidazo[1,2-a]pyridine-7-carboxylic acid, was converted to the title compound (56 mg, 78%) which was obtained as a light yellow solid. MS: m/e=359.1 $[M+H]^+$.

EXAMPLE 34

2-(5-Methyl-3-phenyl-isoxazol-4-yl)-imidazo[1,2-a]
pyridine-6-carboxylic acid cyclobutylamide As described for Example 14, 2-(5-methyl-3-phenyl-isoxazol-4-yl)-imidazo[1,2-a]pyridine-6-carboxylic acid (96 mg, 0.3 mmol), instead of 2-(5-methyl-3-phenyl-isoxazol-4-yl)-imidazo[1,2-a]pyridine-7-carboxylic acid, was converted to the title compound (92 mg, 82%) which was obtained as a light yellow foam. MS: m/e=373.3 $[M+H]^+$.

EXAMPLE 35

2-(5-Methyl-3-phenyl-isoxazol-4-yl)-imidazo[1,2-a]
pyridine-6-carboxylic acid cyclopentylamide As described for Example 15, 2-(5-methyl-3-phenyl-isoxazol-4-yl)-imidazo[1,2-a]pyridine-6-carboxylic acid (96 mg, 0.3 mmol), instead of 2-(5-methyl-3-phenyl-isoxazol-4-yl)-imidazo[1,2-a]pyridine-7-carboxylic acid, was converted to the title compound (98 mg, 85%) which was obtained as a light yellow foam. MS: m/e=387.3 $[M+H]^+$.

EXAMPLE 36

2-(5-Methyl-3-phenyl-isoxazol-4-yl)-imidazo[1,2-a]
pyridine-6-carboxylic acid (2-hydroxy-ethyl)-amide As described for Example 16, 2-(5-methyl-3-phenyl-isoxazol-4-yl)-imidazo[1,2-a]pyridine-6-carboxylic acid (96 mg, 0.3 mmol), instead of 2-(5-methyl-3-phenyl-isoxazol-4-yl)-imidazo[1,2-a]pyridine-7-carboxylic acid, was converted to the title compound (86 mg, 79%) which was obtained as a light yellow foam. MS: m/e=363.3 $[M+H]^+$.

EXAMPLE 37

2-(5-Methyl-3-phenyl-isoxazol-4-yl)-imidazo[1,2-a]
pyridine-6-carboxylic acid (tetrahydro-pyran-4-yl)-
amide As described for Example 17, 2-(5-methyl-3-phenyl-isoxazol-4-yl)-imidazo[1,2-a]pyridine-6-carboxylic acid (64 mg, 0.2 mmol), instead of 2-(5-methyl-3-phenyl-isoxazol-4-yl)-imidazo[1,2-a]pyridine-7-carboxylic acid, was converted to the title compound (61 mg, 76%) which was obtained as an off white solid. MS: m/e=403.5 $[M+H]^+$.

EXAMPLE 38

2-(5-Methyl-3-phenyl-isoxazol-4-yl)-imidazo[1,2-a]
pyridine-6-carboxylic acid (2-morpholin-4-yl-ethyl)-
amide As described for Example 18, 2-(5-methyl-3-phenyl-isoxazol-4-yl)-imidazo[1,2-a]pyridine-6-carboxylic acid (64 mg, 0.2 mmol), instead of 2-(5-methyl-3-phenyl-isoxazol-4-yl)-imidazo[1,2-a]pyridine-7-carboxylic acid, was converted to the title compound (56 mg, 65%) which was obtained as a light yellow foam. MS: m/e=432.5 $[M+H]^+$.

EXAMPLE 39

2-(5-Methyl-3-phenyl-isoxazol-4-yl)-imidazo[1,2-a]
pyridine-6-carboxylic acid (3-morpholin-4-yl-pro-
pyl)-amide As described for Example 19, 2-(5-methyl-3-phenyl-isoxazol-4-yl)-imidazo[1,2-a]pyridine-6-carboxylic acid (96 mg, 0.3 mmol), instead of 2-(5-methyl-3-phenyl-isoxazol-4-yl)-imidazo[1,2-a]pyridine-7-carboxylic acid, was converted to the title compound (117 mg, 88%) which was obtained as an off white foam. MS: m/e=410.1 $[M+H]^+$.

EXAMPLE 40

2-(5-Methyl-3-phenyl-isoxazol-4-yl)-imidazo[1,2-a]
pyridine-6-carboxylic acid (pyridin-2-ylmethyl)-
amide As described for Example 20, 2-(5-methyl-3-phenyl-isoxazol-4-yl)-imidazo[1,2-a]pyridine-6-carboxylic acid (96 mg, 0.3 mmol), instead of 2-(5-methyl-3-phenyl-isoxazol-4-yl)-imidazo[1,2-a]pyridine-7-carboxylic acid, was converted to the title compound (108 mg, 88%) which was obtained as a yellow foam. MS: m/e=410.3 $[M+H]^+$.

EXAMPLE 41

2-(5-Methyl-3-phenyl-isoxazol-4-yl)-imidazo[1,2-a]
pyridine-6-carboxylic acid (pyridin-3-ylmethyl)-
amide As described for Example 21, 2-(5-methyl-3-phenyl-isoxazol-4-yl)-imidazo[1,2-a]pyridine-6-carboxylic acid (64 mg, 0.2 mmol), instead of 2-(5-methyl-3-phenyl-isoxazol-4-yl)-imidazo[1,2-a]pyridine-7-carboxylic acid, was converted to the title compound (67 mg, 82%) which was obtained as a light yellow foam. MS: m/e=410.3 $[M+H]^+$.

EXAMPLE 42

2-(5-Methyl-3-phenyl-isoxazol-4-yl)-imidazo[1,2-a]
pyridine-6-carboxylic acid (pyridin-4-ylmethyl)-
amide As described for Example 22, 2-(5-methyl-3-phenyl-isoxazol-4-yl)-imidazo[1,2-a]pyridine-6-carboxylic acid (96 mg, 0.3 mmol), instead of 2-(5-methyl-3-phenyl-isoxazol-4-yl)-imidazo[1,2-a]pyridine-7-carboxylic acid, was converted to the title compound (105 mg, 86%) which was obtained as an off white solid. MS: m/e=410.1 $[M+H]^+$.

EXAMPLE 43

2-(5-Methyl-3-phenyl-isoxazol-4-yl)-imidazo[1,2-a]
pyridine-6-carboxylic acid (furan-2-ylmethyl)-amide As described for Example 23, 2-(5-methyl-3-phenyl-isoxazol-4-yl)-imidazo[1,2-a]pyridine-6-carboxylic acid (64 mg, 0.2 mmol), instead of 2-(5-methyl-3-phenyl-isoxazol-4-yl)-imidazo[1,2-a]pyridine-7-carboxylic acid, was converted to the title compound (70 mg, 88%) which was obtained as a light yellow foam. MS: m/e=399.1 $[M+H]^+$.

EXAMPLE 44

7-Bromo-2-(5-methyl-3-phenyl-isoxazol-4-yl)-imidazo[1,2-a]pyridine

As described for Example 2, 4-(bromoacetyl)-5-methyl-3-phenylisoxazole (commercially available) (2.0 g, 7.2 mmol) was converted, using 2-amino-4-bromopyridine instead of 2-amino-3-methylpyridine, to the title compound (824 mg, 33%) which was obtained as a light yellow foam. MS: m/e=354.1/355.9 [M+H]$^+$.

EXAMPLE 45

7-Ethynyl-2-(5-methyl-3-phenyl-isoxazol-4-yl)-imidazo[1,2-a]pyridine

A mixture of 7-bromo-2-(5-methyl-3-phenyl-isoxazol-4-yl)-imidazo[1,2-a]pyridine (100 mg, 0.28 mmol) containing trimethylsilylacetylene (80 µL, 0.57 mmol), triethylamine (118 µL, 0.85 mmol), PdCl$_2$(PPh$_3$)$_2$ (9.9 mg, 0.014 mmol) and PPh$_3$ (2.2 mg, 0.08 mmol) in THF (1 mL) was purged for 10 min with argon. Then CuI (0.5 mg, 0.003 mmol) was added and the reaction mixture was heated up to 60° C. and stirring was continued for 3 h.

The mixture was then poured into cold hydrochloric acid (1 M) and extracted with ethyl acetate. The combined organic layers were then washed with water and brine, dried over sodium sulphate and evaporated to leave a yellow oil. Purification by chromatography (SiO$_2$, heptane:ethyl acetate=100:0 to 70:30) afforded 2-(5-methyl-3-phenyl-isoxazol-4-yl)-7-trimethylsilanylethynyl-imidazo[1,2-a]pyridine (86 mg, 82%) which was obtained as a yellow foam. MS: m/e=372.1 [M+H]$^+$. Then 2-(5-methyl-3-phenyl-isoxazol-4-yl)-7-trimethylsilanylethynyl-imidazo[1,2-a]pyridine (81 mg, 0.22 mmol) was dissolved in methanol (1 mL), a spatula tip of potassium carbonate was added at 0° C. and the reaction mixture was stirred at room temperature for 2 h. The mixture was then poured into brine and extracted with ethyl acetate. The combined organic layers were then washed with water and brine, dried over sodium sulphate and evaporated to leave a brown oil. Purification by chromatography (SiO$_2$, heptane:ethyl acetate=100:0 to 70:30) afforded the title compound (53 mg, 81%) which was obtained as a yellow foam. MS: m/e=300.3 [M+H]$^+$.

EXAMPLE 46

2-(5-Methyl-3-phenyl-isoxazol-4-yl)-imidazo[1,2-a]pyridin-7-ylamine a) [2-(5-Methyl-3-phenyl-isoxazol-4-yl)-imidazo[1,2-a]pyridin-7-yl]-carbamic acid tert-butyl ester A mixture of 2-(5-methyl-3-phenyl-isoxazol-4-yl)-imidazo[1,2-a]pyridine-7-carboxylic acid (2.93 g, 9.2 mmol) in tert-butanol (34 mL) containing diphenylphosphoryl azide (2.53 g, 9.2 mmol) and tiethylamine was heated under reflux for 3 h. After cooling to room temperature, the mixture was poured onto a saturated solution of ammonium chloride and extracted with ethyl acetate. The combined organic layers were then washed with a saturated solution of sodium hydrogen carbonate, brine and then dried over sodium sulphate and evaporated to leave a brown solid. Purification by chromatography (SiO$_2$, heptane:ethyl acetate=100:0 to 25:75) afforded the title compound (1.01 mg, 28%) which was obtained as a light brown solid. MS: m/e=391.4 [M+H]$^+$.

b) 2-(5-Methyl-3-phenyl-isoxazol-4-yl)-imidazo[1,2-a]pyridin-7-ylamine

A mixture of [2-(5-methyl-3-phenyl-isoxazol-4-yl)-imidazo[1,2-a]pyridin-7-yl]-carbamic acid tert-butyl ester (1.0 g, 2.56 mmol) in hydrochloric acid (4 M in dioxane, 29 mL) was stirred at room temperature for 6 h. The precipitate was then filtered off and dissolved in a dilute solution of sodium hydrogen carbonate and then extracted with ethyl acetate. The organic layer was then washed with brine and then dried over sodium sulphate and evaporated to leave a brown foam. Purification by chromatography (SiO$_2$, heptane:ethyl acetate=100:0 to 25:75) afforded the title compound (477 mg, 64%) which was obtained as a light brown foam. MS: m/e=291.1 [M+H]$^+$.

EXAMPLE 47

N-[2-(5-Methyl-3-phenyl-isoxazol-4-yl)-imidazo[1,2-a]pyridin-7-yl]-2-pyridin-3-yl-acetamide A solution of 2-(5-methyl-3-phenyl-isoxazol-4-yl)-imidazo[1,2-a]pyridin-7-ylamine (92 mg, 0.32 mmol) in DMF (0.2 mL) was added to a solution containing 3-pyridylacetic acid (39.5 mg, 0.29 mmol), N,N,N',N'-tetramethyl-O-(benzotriazol-1-yl)uranium tetrafluoroborate (101.7 mg, 0.32 mmol), N,N-diisopropyl ethyl amine (247 µL, 1.44 mmol) in DMF (0.3 mL) and the resulting mixture stirred at room temperature overnight and then heated at 110° C. for 6 h. The resulting mixture was then poured into a mixture of brine: water (1:1) and extracted with ethyl acetate. The combined organic layers were then washed with brine, dried over sodium sulphate and evaporated to leave a brown solid. Purification by chromatography (SiO$_2$, dichloromethane:methanol=90:10) afforded the title compound (4.3 mg, 4%) which was obtained as a yellow oil. MS: m/e=410.1 [M+H]$^+$.

EXAMPLE 48

Cyclopropanecarboxylic acid [2-(5-methyl-3-phenyl-isoxazol-4-yl)-imidazo[1,2-a]pyridin-7-yl]-amide A solution of 2-(5-methyl-3-phenyl-isoxazol-4-yl)-imidazo[1,2-a]pyridin-7-ylamine (92 mg, 0.32 mmol) in DMF (0.2 mL) was added to a solution containing cyclopropanecarboxylic acid (24.8 mg, 0.29 mmol), N,N,N',N'-tetramethyl-O-(benzotriazol-1-yl)uranium tetrafluoroborate (101.7 mg, 0.32 mmol), N,N-diisopropyl ethyl amine (247 µL, 1.44 mmol) in DMF (0.3 mL) and the resulting mixture stirred at room temperature overnight and then heated at 110° C. for 2.5 h. The resulting mixture was then poured into a mixture of brine: water (1:1) and extracted with ethyl acetate. The combined organic layers were then washed with brine, dried over sodium sulphate and evaporated to leave a brown solid. Purification by chromatography (SiO$_2$, heptane:ethyl acetate=100:0 to 0:100) afforded the title compound (12.4 mg, 12%) which was obtained as an off-white solid. MS: m/e 359.0 [M+H]$^+$.

EXAMPLE 49

Cyclobutanecarboxylic acid [2-(5-methyl-3-phenyl-isoxazol-4-yl)-imidazo[1,2-a]pyridin-7-yl]-amide As described for Example 47, 2-(5-methyl-3-phenyl-isoxazol-4-yl)-imidazo[1,2-a]pyridin-7-ylamine (92 mg, 0.32 mmol) was converted, using cyclobutanecarboxylic acid instead of 3-pyridylacetic acid, to the title compound (16.4 mg, 15%) which was obtained as an off-white solid. MS: m/e=373.3 [M+H]$^+$.

EXAMPLE 50

Cyclopentanecarboxylic acid [2-(5-methyl-3-phenyl-isoxazol-4-yl)-imidazo[1,2-a]pyridin-7-yl]-amide As described for Example 47, 2-(5-methyl-3-phenyl-isoxazol-4-yl)-imidazo[1,2-a]pyridin-7-ylamine (92 mg, 0.32 mmol) was converted, using cyclopentanecarboxylic acid instead of 3-pyridylacetic acid, to the title compound (11.1 mg, 10%) which was obtained as an off-white solid. MS: m/e=387.1 [M+H]$^+$.

EXAMPLE 51

N-[2-(5-Methyl-3-phenyl-isoxazol-4-yl)-imidazo[1,2-a]pyridin-7-yl]-nicotinamide

As described for Example 48, 2-(5-methyl-3-phenyl-isoxazol-4-yl)-imidazo[1,2-a]pyridin-7-ylamine (92 mg, 0.32 mmol) was converted, using nicotinic acid instead of cyclopropanecarboxylic acid, to the title compound (19.4 mg, 14%) which was obtained as an off-white solid. MS: m/e=396.0 [M+H]$^+$.

EXAMPLE 52

6-Iodo-2-(5-methyl-3-phenyl-isoxazol-4-yl)-imidazo[1,2-a]pyridine

A mixture of 4-(bromoacetyl)-5-methyl-3-phenylisoxazole (commercially available) (420 mg, 1.5 mmol) and 2-amino-5-iodopyridine (330 mg, 1.5 mmol) in ethanol (6.7 mL) containing hydrobromic acid (48%, 84 μL, 0.75 mmol) and triethylamine (105 μL, 0.75 mmol) was heated under reflux under argon overnight. After cooling to room temperature, the mixture was evaporated and poured onto hydrochloric acid (0.5 N) and extracted with ethyl acetate. The combined organic layers were then washed with water and brine, dried over sodium sulphate and evaporated to leave a yellow oil. Purification by chromatography (SiO$_2$, dichloromethane:methanol=100:0 to 95:5) afforded the title compound (170 mg, 28%) which was obtained as a light yellow solid. MS: m/e=402.1 [M+H]$^+$.

EXAMPLE 53

6-Ethynyl-2-(5-methyl-3-phenyl-isoxazol-4-yl)-imidazo[1,2-a]pyridine

As described for Example 45, 6-bromo-2-(5-methyl-3-phenyl-isoxazol-4-yl)-imidazo[1,2-a]pyridine (100 mg, 0.28 mmol) instead of 7-bromo-2-(5-methyl-3-phenyl-isoxazol-4-yl)-imidazo[1,2-a]pyridine, was converted to 2-(5-methyl-3-phenyl-isoxazol-4-yl)-6-trimethylsilanylethynyl-imidazo[1,2-a]pyridine (39 mg, 37% MS: m/e=372.1 [M+H]$^+$) and then to the title compound (19 mg, 69%) which was obtained as a light yellow foam. MS: m/e=300.3 [M+H]$^+$.

EXAMPLE 54

2-(5-Methyl-3-phenyl-isoxazol-4-yl)-imidazo[1,2-a]pyridin-6-ylamine

As described for Example 46, 2-(5-methyl-3-phenyl-isoxazol-4-yl)-imidazo[1,2-a]pyridine-6-carboxylic acid (1.62 g, 5.1 mmol) instead of 2-(5-methyl-3-phenyl-isoxazol-4-yl)-imidazo[1,2-a]pyridine-7-carboxylic acid, was converted to [2-(5-methyl-3-phenyl-isoxazol-4-yl)-imidazo[1,2-a]pyridin-6-yl]-carbamic acid tert-butyl ester (910 mg, 46% MS: m/e=389.5 [M+H]$^+$) and then to the title compound (506 mg, 78%) which was obtained as a light grey foam. MS: m/e=291.0 [M−H]$^−$.

EXAMPLE 55

2-Cyclopropyl-N-[2-(5-methyl-3-phenyl-isoxazol-4-yl)-imidazo[1,2-a]pyridin-6-yl]-acetamide A solution of 2-(5-methyl-3-phenyl-isoxazol-4-yl)-imidazo[1,2-a]pyridin-6-ylamine (63.9 mg, 0.22 mmol) in DMF (0.2 mL) was added to a solution containing of cyclopropylacetic acid (20 μL, 0.22 mmol), N,N,N',N'-tetramethyl-O-(benzotriazol-1-yl)uranium tetrafluoroborate (70.6 mg, 0.22 mmol), N,N-diisopropyl ethyl amine (129 μL, 1.0 mmol) in DMF (0.3 mL) and the resulting mixture stirred at room temperature for 2 h. The resulting mixture was then poured into a mixture of brine:water (1:1) and extracted with ethyl acetate. The combined organic layers were then washed with brine, dried over sodium sulphate and evaporated to leave a brown solid. Purification by chromatography (SiO$_2$, heptane:ethyl acetate=100:0 to 50:50) afforded the title compound (44 mg, 59%) which was obtained as a light green solid. MS: m/e=373.3 [M+H]$^+$.

EXAMPLE 56

N-[2-(5-Methyl-3-phenyl-isoxazol-4-yl)-imidazo[1,2-a]pyridin-6-yl]-2-pyridin-3-yl-acetamide As described for Example 56, 2-(5-methyl-3-phenyl-isoxazol-4-yl)-imidazo[1,2-a]pyridin-6-ylamine (96 mg, 0.33 mmol) was converted, using 3-pyridylacetic acid instead of cyclopropylacetic acid, to the title compound (26 mg, 42%) which was obtained as a light brown solid. MS: m/e=410.0 [M+H]$^+$.

EXAMPLE 57

Cyclopropanecarboxylic acid [2-(5-methyl-3-phenyl-isoxazol-4-yl)-imidazo[1,2-a]pyridin-6-yl]-amide As described for Example 56, 2-(5-methyl-3-phenyl-isoxazol-4-yl)-imidazo[1,2-a]pyridin-6-ylamine (64 mg, 0.2 mmol) was converted, using cyclopropancarboxylic acid instead of cyclopropylacetic acid, to the title compound (57 mg, 79%) which was obtained as a light brown solid. MS: m/e=359.1 [M+H]$^+$.

EXAMPLE 58

Cyclobutanecarboxylic acid [2-(5-methyl-3-phenyl-isoxazol-4-yl)-imidazo[1,2-a]pyridin-6-yl]-amide As described for Example 56, 2-(5-methyl-3-phenyl-isoxazol-4-yl)-imidazo[1,2-a]pyridin-6-ylamine (96 mg, 0.33 mmol) was converted, using cyclobutanecarboxylic acid instead of cyclopropylacetic acid, to the title compound (33 mg, 30%) which was obtained as a light brown foam. MS: m/e=373.1 [M+H]$^+$.

EXAMPLE 59

Cyclopentanecarboxylic acid [2-(5-methyl-3-phenyl-isoxazol-4-yl)-imidazo[1,2-a]pyridin-6-yl]-amide As described for Example 56, 2-(5-methyl-3-phenyl-isoxazol-4-yl)-imidazo[1,2-a]pyridin-6-ylamine (96 mg, 0.33 mmol) was converted, using cyclopentanecarboxylic acid instead of cyclopropylacetic acid, to the title compound (56 mg, 48%) which was obtained as an off-white solid. MS: m/e=387.3 [M+H]$^+$.

EXAMPLE 60

N-[2-(5-Methyl-3-phenyl-isoxazol-4-yl)-imidazo[1,2-a]pyridin-6-yl]-benzamide

A microwave tube containing 6-iodo-2-(5-methyl-3-phenyl-isoxazol-4-yl)-imidazo[1,2-a]pyridine (100 mg, 0.25 mmol), benzamide (30 mg, 0.25 mmol) and cesium carbonate (162 mg, 0.5 mmol) in DMF (1.2 mL) was evacuated and then back-filled with Ar several time and then sealed. The resulting mixture was heated to 150° C. in the microwave for 3 h and then additional benzamide (30 mg, 0.25 mmol) and CuI (5 mg, 0.025 mmol) added and the resulting mixture heated to 200° C. in the microwave (2×30 min). The resulting mixture was then poured into water and extracted with ethyl acetate. The combined organic layers were then washed with brine, dried over sodium sulphate and evaporated to leave a brown gum. Purification by chromatography (SiO$_2$, heptane:ethyl acetate=100:0 to 25:75) afforded a solid that was then diluted with hydrochloric acid (1 N) and ethyl acetate. The precipitate was filtered off to afford the title compound (12.1 mg, 12%) which was obtained as a light yellow solid. MS: m/e=395.0 [M+H]$^+$.

EXAMPLE 61

N-[2-(5-Methyl-3-phenyl-isoxazol-4-yl)-imidazo[1,2-a]pyridin-6-yl]-nicotinamide

As described for Example 56, 2-(5-methyl-3-phenyl-isoxazol-4-yl)-imidazo[1,2-a]pyridin-6-ylamine (71 mg, 0.22 mmol) was converted, using nicotinic acid instead of cyclopropylacetic acid, to the title compound (63 mg, 80%) which was obtained as an off-white solid. MS: m/e=396.3 [M+H]$^+$.

EXAMPLE 62

1-[2-(5-Methyl-3-phenyl-isoxazol-4-yl)-imidazo[1,2-a]pyridin-6-yl]-azetidin-2-one As described for Example 60, 6-iodo-2-(5-methyl-3-phenyl-isoxazol-4-yl)-imidazo[1,2-a]pyridine (100 mg, 0.25 mmol) was converted, using 2-azetidinone instead of benzamide, to the title compound (4.8 mg, 6%) which was obtained as a light yellow oil. MS: m/e=345.0 [M+H]$^+$.

EXAMPLE 63

1-[2-(5-Methyl-3-phenyl-isoxazol-4-yl)-imidazo[1,2-a]pyridin-6-yl]-pyrrolidin-2-one As described for Example 60, 6-iodo-2-(5-methyl-3-phenyl-isoxazol-4-yl)-imidazo[1,2-a]pyridine (135 mg, 0.34 mmol) was converted, using 2-pyrrolidone instead of benzamide, to the title compound (61 mg, 51%) which was obtained as a light brown solid. MS: m/e=359.0 [M+H]$^+$.

EXAMPLE 64

2-(5-Methyl-3-phenyl-isoxazol-4-yl)-6-pyrrol-1-yl-imidazo[1,2-a]pyridine

As described for Example 60, 6-iodo-2-(5-methyl-3-phenyl-isoxazol-4-yl)-imidazo[1,2-a]pyridine (80 mg, 0.2 mmol) was converted, using pyrrole instead of benzamide, to the title compound (5 mg, 7%) which was obtained as a light yellow solid. MS: m/e=341.3 [M+H]$^+$.

EXAMPLE 65

2-(5-Methyl-3-phenyl-isoxazol-4-yl)-6-pyrazol-1-yl-imidazo[1,2-a]pyridine

As described for Example 60, 6-bromo-2-(5-methyl-3-phenyl-isoxazol-4-yl)-imidazo[1,2-a]pyridine (70.8 mg, 0.2 mmol) instead of 6-iodo-2-(5-methyl-3-phenyl-isoxazol-4-yl)-imidazo[1,2-a]pyridine was converted, using pyrazole instead of benzamide, to the title compound (11 mg, 16%) which was obtained as a light yellow gum. MS: m/e=342.3 [M+H]$^+$.

EXAMPLE 66

6-Imidazol-1-yl-2-(5-methyl-3-phenyl-isoxazol-4-yl)-imidazo[1,2-a]pyridine

As described for Example 60, 6-iodo-2-(5-methyl-3-phenyl-isoxazol-4-yl)-imidazo[1,2-a]pyridine (47 mg, 0.13 mmol) was converted, using imidazole instead of benzamide, to the title compound (13 mg, 29%) which was obtained as a brown foam. MS: m/e=342.3 [M+H]$^+$ as the most polar component.

EXAMPLE 67

5-Imidazol-1-yl-2-(5-methyl-3-phenyl-isoxazol-4-yl)-imidazo[1,2-a]pyridine

As described for Example 66, 6-iodo-2-(5-methyl-3-phenyl-isoxazol-4-yl)-imidazo[1,2-a]pyridine (47 mg, 0.13 mmol) was converted to the title compound (8 mg, 18%) which was obtained as a yellow gum. MS: m/e=342.1 [M+H]$^+$ as the least polar component.

EXAMPLE 68

2-(5-Cyclopropyl-3-phenyl-isoxazol-4-yl)-imidazo[1,2-a]pyridine a) 5-Cyclopropyl-3-phenyl-isoxazole-4-carboxylic acid ethyl ester To a solution of N-hydroxybenzenecarboximidoyl chloride (*Tetrahedron Letters*, 47(9), 1457-1460, 2006, 500 mg, 3.21 mmol) and cyclopropyl-propynoic acid ethyl ester (*Organic Syntheses*, 66, 173-179, 1988, 515 mg, 3.21 mmol) in diethyl ether (5 ml) was added dropwise over a period of 2 min at ambient temperature triethylamine (0.54 ml, 3.86 mmol) and the reaction mixture was stirred for 3 d at this temperature. The resulting suspension was diluted with tert-butylmethylether (5 ml) and water (10 ml). The aqueous layer was extracted with tert-butylmethylether (10 ml) and the organic layers were washed with water (10 ml) and brine (10 ml). Drying over sodium sulfate and purification by chromatography (SiO$_2$, heptane:ethyl acetate=98:2 to 80:20) afforded the title compound (414 mg, 50%) as a colorless liquid. MS: m/e=258.1 [M+H]$^+$.

b) 5-Cyclopropyl-3-phenyl-isoxazole-4-carboxylic acid

To a solution of 5-cyclopropyl-3-phenyl-isoxazole-4-carboxylic acid ethyl ester (408 mg, 1.58 mmol) in ethanol (4 ml) was added aqueous sodium hydroxide (1 N, 3.17 ml, 3.17 mmol) and the mixture was stirred for 3 h at 80° C. The ethanol was distilled off and the residue diluted with water (5 ml) and acified with aqueous HCl (1N) to pH=1. The resulting suspension was filtered off and washed with water affording the title compound (314 mg, 86%) as a white solid. MS: m/e=230.3[M+H]$^+$.

c) 5-Cyclopropyl-3-phenyl-isoxazole-4-carboxylic acid methoxy-methyl-amide

A mixture of 5-cyclopropyl-3-phenyl-isoxazole-4-carboxylic acid (3.72 g, 16 mmol), N,O-dimethylhydroxylamine hydrochloride (2.53 g, 26 mmol), N-methylmorpholine (2.85 mL, 26 mmol) and 4-dimethylaminopyridine (198 mg, 2 mmol) in dichloromethane (50 mL) and DMF (10 mL) was cooled to 0° C. Then 1-(3-dimethylaminopropyl)-3-ethylcarbodiimide (3.73 g, 19 mmol) was added and the reaction mixture was stirred at room temperature for 2 h. The reaction mixture was poured into hydrochloric acid (1 N ) and extracted with ethyl acetate. The combined organic layers were then washed with a saturated solution of sodium hydrogen carbonate, brine and then dried over sodium sulphate and evaporated to leave a light yellow oil. Purification by chromatography (SiO$_2$, heptane:ethyl acetate=100:0 to 50:50) afforded the title compound (4.03 g, 91%) which was obtained as a courses oil. MS: m/e=273.0 [M+H]$^+$.

d) 1-(5-Cyclopropyl-3-phenyl-isoxazol-4-yl)-ethanone

To a solution of 5-cyclopropyl-3-phenyl-isoxazole-4-carboxylic acid methoxy-methyl-amide (4.00 g, 14.7 mmol) in THF (42 mL) cooled to −78° C. was added a solution of methylmagnesium bromide (3 M in diethylether, 9.80 mL, 29.4 mmol) dropwise within 5 min at −78° C. The cooling bath was removed and the reaction mixture was allowed to warm up to room temperature over 2.5 h. The reaction mixture was then re-cooled to −78° C., diluted with a saturated ammonium chloride solution (50 mL), allowed to warm up to room temperature and then diluted with water and extracted with ethyl acetate. The combined organic layers were then washed with brine and then dried over sodium sulphate and evaporated to afford the title compound (3.2 g, 94%) which was obtained as a light yellow solid. MS: m/e=228.3 [M+H]$^+$.

e) 2-Bromo-1-(5-cyclopropyl-3-phenyl-isoxazol-4-yl)-ethanone

To a solution of 1-(5-cyclopropyl-3-phenyl-isoxazol-4-yl)-ethanone (3.34 g, 14.6 mmol) in carbontetrachloride (9.7 mL) and AcOH (0.4 mL) at 48° C. was added a solution of bromine (0.79 mL, 14.6 mmol) in carbontetrachloride (7.8 mL) over 10 min keeping the temperature below 50° C. After addition the reaction mixture was allowed to cool down to room temperature and poured into ice-water (50 mL). The layers were separated and the aqueous layer extracted with dichloromethane. The combined organic layers were then washed with water and brine, dried over sodium sulphate and evaporated. Purification by chromatography (SiO$_2$, heptane: ethyl acetate: 100:0 to 80:20) afforded the title compound (4.29 g, 95%) which was obtained as an off-white solid. MS m/e (EI): 305.0/307.0 [M].

f) 2-(5-Cyclopropyl-3-phenyl-isoxazol-4-yl)-imidazo[1,2-a]pyridine

A mixture of 2-bromo-1-(5-cyclopropyl-3-phenyl-isoxazol-4-yl)-ethanone (91.8mg, 0.3 mmol) and 2-aminopyridine (28.2 mg, 0.3 mmol) in ethanol (2 mL) containing hydrobromic acid (48%, 16.9 µL, 0.8 mmol) was heated under reflux under argon for 2 h. Another portion of 2-aminopyridine (28.2 mg, 0.3 mmol) was added and heating continued under reflux under argon for 1 h. After cooling to room temperature, the mixture was evaporated and poured onto saturated sodium hydrogen carbonate and extracted with ethyl acetate. The combined organic layers were then washed with water and brine, dried over sodium sulphate and evaporated to leave a yellow oil. Purification by chromatography (SiO$_2$, heptane:ethyl acetate: 100:0 to 50:50) afforded the title compound (49 mg, 54%) which was obtained as an off-white solid. MS: m/e=302.1 [M+H]$^+$.

EXAMPLE 69

6-Bromo-2-(5-cyclopropyl-3-phenyl-isoxazol-4-yl)-imidazo[1,2-a]pyridine

As described for Example 27, 2-bromo-1-(5-cyclopropyl-3-phenyl-isoxazol-4-yl)-ethanone (91 .8mg, 0.3 mmol) instead of 4-(bromoacetyl)-5-methyl-3-phenylisoxazole was converted to the title compound (14 mg, 12%) which was obtained as a light yellow solid. MS: m/e=380.0/382.0 [M+H]$^+$.

The invention claimed is:

1. An aryl-isoxazol-4-yl-imidazo[1,2-a]pyridine derivative of formula I

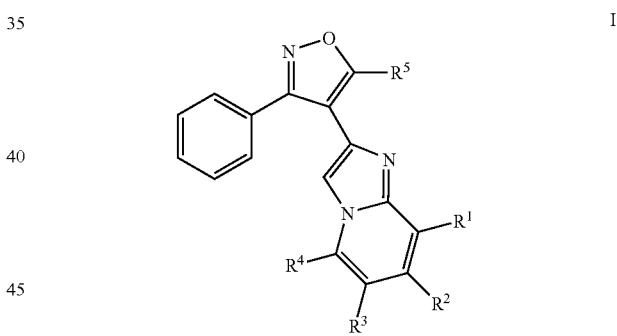

I wherein
  $R^1$ is hydrogen, halogen, hydroxy, lower alkyl, benzyloxy or —O—(CH$_2$)—(CO)-5 or 6 membered heteroaryl optionally substituted by aryl or by lower alkyl;
  $R^2$ is hydrogen, halogen, lower alkyl, lower alkynyl, amino, —NHC(O)—R$^a$ or —(CO)—R$^a$;
  $R^3$ is hydrogen, halogen, cyano, lower alkyl, lower alkynyl, amino, —NHC(O)—R$^a$, —(CO)—R$^a$, -5 or 6-membered heterocycloalkyl in the 1-position, optionally substituted by =O or is a -5 or 6-membered heteroaryl in the 1-position;
  $R^4$ is hydrogen or -5 or 6-membered heteroaryl;
  $R^5$ is lower alkyl or cycloalkyl;
  $R^a$ is lower alkoxy or NR'R", wherein R' and R" are each independently hydrogen, lower alkyl optionally substituted by hydroxy, lower alkynyl, —(CH$_2$)$_n$-cycloalkyl, —(CH$_2$)$_n$-5 or 6-membered heterocycloalkyl or —(CH$_2$)$_n$-5 or 6-membered heteroaryl; and
  n is 0 to 3;

or a pharmaceutically acceptable acid addition salt thereof.

2. The compound of claim 1, wherein $R^3$ is hydrogen.

3. The compound of claim 2, selected from the group consisting of
- 2-(5-methyl-3-phenyl-isoxazol-4-yl)-imidazo[1,2-a]pyridine;
- 8-methyl-2-(5-methyl-3-phenyl-isoxazol-4-yl)-imidazo[1,2-a]pyridine;
- 8-chloro-2-(5-methyl-3-phenyl-isoxazol-4-yl)-imidazo[1,2-a]pyridine;
- 8-bromo-2-(5-methyl-3-phenyl-isoxazol-4-yl)-imidazo[1,2-a]pyridine;
- 2-(5-methyl-3-phenyl-isoxazol-4-yl)-imidazo[1,2-a]pyridin-8-ol;
- 8-benzyloxy-2-(5-methyl-3-phenyl-isoxazol-4-yl)-imidazo[1,2-a]pyridine;
- 1-(5-methyl-3-phenyl-isoxazol-4-yl)-2-[2-(5-methyl-3-phenyl-isoxazol-4-yl)-imidazo[1,2-a]pyridin-8-yloxy]-ethanone;
- 7-methyl-2-(5-methyl-3-phenyl-isoxazol-4-yl)-imidazo[1,2-a]pyridine;
- 7-ethyl-2-(5-methyl-3-phenyl-isoxazol-4-yl)-imidazo[1,2-a]pyridine; and
- 2-(5-methyl-3-phenyl-isoxazol-4-yl)-imidazo[1,2-a]pyridine-7-carboxylic acid methyl ester.

4. The compound of claim 2, selected from the group consisting of
- 2-(5-methyl-3-phenyl-isoxazol-4-yl)-imidazo[1,2-a]pyridine-7-carboxylic acid cyclopropylmethyl-amide;
- 2-(5-methyl-3-phenyl-isoxazol-4-yl)-imidazo[1,2-a]pyridine-7-carboxylic acid prop-2-ynylamide;
- 2-(5-methyl-3-phenyl-isoxazol-4-yl)-imidazo[1,2-a]pyridine-7-carboxylic acid cyclopropylamide;
- 2-(5-methyl-3-phenyl-isoxazol-4-yl)-imidazo[1,2-a]pyridine-7-carboxylic acid cyclobutylamide;
- 2-(5-methyl-3-phenyl-isoxazol-4-yl)-imidazo[1,2-a]pyridine-7-carboxylic acid cyclopentylamide;
- 2-(5-methyl-3-phenyl-isoxazol-4-yl)-imidazo[1,2-a]pyridine-7-carboxylic acid (2-hydroxy-ethyl)-amide;
- 2-(5-methyl-3-phenyl-isoxazol-4-yl)-imidazo[1,2-a]pyridine-7-carboxylic acid (tetrahydro-pyran-4-yl)-amide;
- 2-(5-methyl-3-phenyl-isoxazol-4-yl)-imidazo[1,2-a]pyridine-7-carboxylic acid (2-morpholin-4-yl-ethyl)-amide;
- 2-(5-methyl-3-phenyl-isoxazol-4-yl)-imidazo[1,2-a]pyridine-7-carboxylic acid (3-morpholin-4-yl-propyl)-amide; and
- 2-(5-methyl-3-phenyl-isoxazol-4-yl)-imidazo[1,2-a]pyridine-7-carboxylic acid (pyridin-2-ylmethyl)-amide.

5. The compound of claim 2, selected from the group consisting of
- 2-(5-methyl-3-phenyl-isoxazol-4-yl)-imidazo[1,2-a]pyridine-7-carboxylic acid (pyridin-3-ylmethyl)-amide;
- 2-(5-methyl-3-phenyl-isoxazol-4-yl)-imidazo[1,2-a]pyridine-7-carboxylic acid (pyridin-4-ylmethyl)-amide;
- 2-(5-methyl-3-phenyl-isoxazol-4-yl)-imidazo[1,2-a]pyridine-7-carboxylic acid (furan-2-ylmethyl)-amide;
- 7-bromo-2-(5-methyl-3-phenyl-isoxazol-4-yl)-imidazo[1,2-a]pyridine;
- 7-ethynyl-2-(5-methyl-3-phenyl-isoxazol-4-yl)-imidazo[1,2-a]pyridine;
- 2-(5-methyl-3-phenyl-isoxazol-4-yl)-imidazo[1,2-a]pyridin-7-ylamine;
- N-[2-(5-methyl-3-phenyl-isoxazol-4-yl)-imidazo[1,2-a]pyridin-7-yl]-2-pyridin-3-yl-acetamide;
- cyclopropanecarboxylic acid [2-(5-methyl-3-phenyl-isoxazol-4-yl)-imidazo[1,2-a]pyridin-7-yl]-amide;
- cyclobutanecarboxylic acid [2-(5-methyl-3-phenyl-isoxazol-4-yl)-imidazo[1,2-a]pyridin-7-yl]-amide;
- cyclopentanecarboxylic acid [2-(5-methyl-3-phenyl-isoxazol-4-yl)-imidazo[1,2-a]pyridin-7-yl]-amide and
- N-[2-(5-methyl-3-phenyl-isoxazol-4-yl)-imidazo[1,2-a]pyridin-7-yl]-nicotinamide.

6. The compound of claim 1, wherein $R^3$ is halogen.

7. The compound of claim 6, selected from the group consisting of
- 6-fluoro-2-(5-methyl-3-phenyl-isoxazol-4-yl)-imidazo[1,2-a]pyridine;
- 6-chloro-2-(5-methyl-3-phenyl-isoxazol-4-yl)-imidazo[1,2-a]pyridine;
- 6-bromo-2-(5-methyl-3-phenyl-isoxazol-4-yl)-imidazo[1,2-a]pyridine;
- 6-Iodo-2-(5-methyl-3-phenyl-isoxazol-4-yl)-imidazo[1,2-a]pyridine and
- 6-bromo-2-(5-cyclopropyl-3-phenyl-isoxazol-4-yl)-imidazo[1,2-a]pyridine.

8. The compound of claim 1, wherein $R^3$ is cyano.

9. The compound of claim 8, which is 2-(5-methyl-3-phenyl-isoxazol-4-yl)-imidazo[1,2-a]pyridine-6-carbonitrile.

10. The compound of claim 1, wherein $R^3$ is lower alkyl.

11. The compound of claim 10, which is 6-methyl-2-(5-methyl-3-phenyl-isoxazol-4-yl)-imidazo[1,2-a]pyridine.

12. The compound of claim 1, wherein $R^3$ is —C(O)—$R^a$, wherein $R^a$ is lower alkoxy or NR'R", wherein R' and R" are each independently hydrogen, lower alkyl optionally substituted by hydroxy, lower alkynyl, —(CH$_2$)$_n$-cycloalkyl, —(CH$_2$)$_n$-5 or 6-membered heterocycloalkyl or —(CH$_2$)$_n$-5 or 6-membered heteroaryl; and n is 0 to 3.

13. The compound of claim 12, selected from the group consisting of:
- 2-(5-methyl-3-phenyl-isoxazol-4-yl)-imidazo[1,2-a]pyridine-6-carboxylic acid methyl ester;
- 2-(5-methyl-3-phenyl-isoxazol-4-yl)-imidazo[1,2-a]pyridine-6-carboxylic acid ethyl ester;
- 2-(5-methyl-3-phenyl-isoxazol-4-yl)-imidazo[1,2-a]pyridine-6-carboxylic acid cyclopropylmethyl-amide;
- 2-(5-methyl-3-phenyl-isoxazol-4-yl)-imidazo[1,2-a]pyridine-6-carboxylic acid prop-2-ynylamide;
- 2-(5-methyl-3-phenyl-isoxazol-4-yl)-imidazo[1,2-a]pyridine-6-carboxylic acid cyclopropylamide;
- 2-(5-methyl-3-phenyl-isoxazol-4-yl)-imidazo[1,2-a]pyridine-6-carboxylic acid cyclobutylamide;
- 2-(5-methyl-3-phenyl-isoxazol-4-yl)-imidazo[1,2-a]pyridine-6-carboxylic acid cyclopentylamide;
- 2-(5-methyl-3-phenyl-isoxazol-4-yl)-imidazo[1,2-a]pyridine-6-carboxylic acid (2-hydroxy-ethyl)-amide;
- 2-(5-methyl-3-phenyl-isoxazol-4-yl)-imidazo[1,2-a]pyridine-6-carboxylic acid (tetrahydro-pyran-4-yl)-amide; and
- 2-(5-methyl-3-phenyl-isoxazol-4-yl)-imidazo[1,2-a]pyridine-6-carboxylic acid (2-morpholin-4-yl-ethyl)-amide.

14. The compound of claim 12, selected from the group consisting of:
- 2-(5-methyl-3-phenyl-isoxazol-4-yl)-imidazo[1,2-a]pyridine-6-carboxylic acid (3-morpholin-4-yl-propyl)-amide;
- 2-(5-methyl-3-phenyl-isoxazol-4-yl)-imidazo[1,2-a]pyridine-6-carboxylic acid (pyridin-2-ylmethyl)-amide;
- 2-(5-methyl-3-phenyl-isoxazol-4-yl)-imidazo[1,2-a]pyridine-6-carboxylic acid (pyridin-3-ylmethyl)-amide;
- 2-(5-methyl-3-phenyl-isoxazol-4-yl)-imidazo[1,2-a]pyridine-6-carboxylic acid (pyridin-4-ylmethyl)-amide; and 2-(5-methyl-3-phenyl-isoxazol-4-yl)-imidazo[1,2-a]pyridine-6-carboxylic acid (furan-2-ylmethyl)-amide.

15. The compound of claim 1, wherein $R^3$ is amino, —NHC(O)—$R^a$, -5 or 6-membered heterocycloalkyl in the 1-position, optionally substituted by =O or is -5 or 6-membered heteroaryl in the 1-position.

16. The compound of claim 15, selected from the group consisting of:

2-(5-methyl-3-phenyl-isoxazol-4-yl)-imidazo[1,2-a]pyridin-6-ylamine;

2-cyclopropyl-N-[2-(5-methyl-3-phenyl-isoxazol-4-yl)-imidazo[1,2-a]pyridin-6-yl]-acetamide;

N-[2-(5-methyl-3-phenyl-isoxazol-4-yl)-imidazo[1,2-a]pyridin-6-yl]-2-pyridin-3-yl-acetamide;

cyclopropanecarboxylic acid [2-(5-methyl-3-phenyl-isoxazol-4-yl)-imidazo[1,2-a]pyridin-6-yl]-amide;

cyclobutanecarboxylic acid [2-(5-methyl-3-phenyl-isoxazol-4-yl)-imidazo[1,2-a]pyridin-6-yl]-amide;

cyclopentanecarboxylic acid [2-(5-methyl-3-phenyl-isoxazol-4-yl)-imidazo[1,2-a]pyridin-6-yl]-amide;

N-[2-(5-methyl-3-phenyl-isoxazol-4-yl)-imidazo[1,2-a]pyridin-6-yl]-benzamide;

N-[2-(5-methyl-3-phenyl-isoxazol-4-yl)-imidazo[1,2-a]pyridin-6-yl]-nicotinamide;

1-[2-(5-methyl-3-phenyl-isoxazol-4-yl)-imidazo[1,2-a]pyridin-6-yl]-azetidin-2-one;

1-[2-(5-methyl-3-phenyl-isoxazol-4-yl)-imidazo[1,2-a]pyridin-6-yl]-pyrrolidin-2-one;

2-(5-methyl-3-phenyl-isoxazol-4-yl)-6-pyrrol-1-yl-imidazo[1,2-a]pyridine;

2-(5-methyl-3-phenyl-isoxazol-4-yl)-6-pyrazol-1-yl-imidazo[1,2-a]pyridine and 6-imidazol-1-yl-2-(5-methyl-3-phenyl-isoxazol-4-yl)-imidazo[1,2-a]pyridine.

* * * * *